(12) United States Patent
Jacob et al.

(10) Patent No.: US 12,239,683 B2
(45) Date of Patent: Mar. 4, 2025

(54) SYNERGISTIC HEPATOPROTECTIVE COMPOSITION

(71) Applicant: FFF BIOWORKS LLP, Bangalore (IN)

(72) Inventors: Avoorathu Thomas Jacob, Bangalore (IN); Jayaraman Bharathi, Bangalore (IN); Thomas Avoorathu Jacob, Bangalore (IN)

(73) Assignee: FFF BIOWORKS LLP, Bangalore (IN)

( * ) Notice: Subject to any disclaimer, the term of this patent is extended or adjusted under 35 U.S.C. 154(b) by 954 days.

(21) Appl. No.: 17/056,394

(22) PCT Filed: Apr. 18, 2019

(86) PCT No.: PCT/IB2019/053227
§ 371 (c)(1),
(2) Date: Nov. 17, 2020

(87) PCT Pub. No.: WO2019/202547
PCT Pub. Date: Oct. 24, 2019

(65) Prior Publication Data
US 2021/0213094 A1    Jul. 15, 2021

(30) Foreign Application Priority Data
Apr. 19, 2018 (IN) .............. 201841010068

(51) Int. Cl.
| | |
|---|---|
| A61K 36/9066 | (2006.01) |
| A23L 33/00 | (2016.01) |
| A23L 33/105 | (2016.01) |
| A61K 9/16 | (2006.01) |
| A61K 31/047 | (2006.01) |

(Continued)

(52) U.S. Cl.
CPC ........ *A61K 36/9066* (2013.01); *A23L 33/105* (2016.08); *A23L 33/40* (2016.08); *A61K 9/1652* (2013.01); *A61K 9/1694* (2013.01); *A61K 31/047* (2013.01); *A61K 36/28* (2013.01); *A61P 1/16* (2018.01); *A61P 3/06* (2018.01); *A23V 2002/00* (2013.01)

(58) Field of Classification Search
None
See application file for complete search history.

(56) References Cited

U.S. PATENT DOCUMENTS

| | | |
|---|---|---|
| 7,090,862 B2 | 8/2006 | Barrett-Reis |
| 2012/0071550 A1 | 3/2012 | Zelkha |

OTHER PUBLICATIONS

Osawa, "Nephroprotective and hepatoprotective effects of curcuminoids" The Molecular Targets and Therapeutic Uses of Curcumin in Health and Disease. 2007.

(Continued)

*Primary Examiner* — Isis A Ghali
(74) *Attorney, Agent, or Firm* — Maschoff Brennan

(57) ABSTRACT

The present invention relates to a synergistic hepatoprotective composition and in particular to a synergistic hepatoprotective composition having a novel combination of the phytochemicals namely curcuminoids and carotenoids such as lutein. The synergistic hepatoprotective composition is effective in promoting health more particularly in protecting normal liver function. Also provided is a novel process for manufacturing such a composition and its use in foods, beverages including alcoholic beverages and as nutraceuticals, dietary supplements and pharmaceuticals.

11 Claims, 14 Drawing Sheets

(51) Int. Cl.
*A61K 36/28* (2006.01)
*A61P 1/16* (2006.01)
*A61P 3/06* (2006.01)

(56) References Cited

OTHER PUBLICATIONS

Sindhu, et al., "Carotenoid lutein protects rats from paracetamol, carbon, tetrachlorideand ethanolinduced hepatic damage" Aug. 2010.
Akram, M, Shahab-uddin, Ahmed, A., Khan, U., Hannan, A., Mohiuddin, E., Asif, M. (2010) Curcuma Longa and Curcumin: A review Article. Rom. J. Biol.—Plant Biol., vol. 55, No. 2, p. 65-70.
Iribarren, C., Folsom, A. R., Jacobs, D. R., Gross, M. D., Belcher, J. D. & Eckfeldt, J. H. (1997) Associations of serum vitamin levels, LDL susceptibility to oxidation, and autoantibodies against MDA-LDL with carotid atherosclerosis. Arterioscler. Thromb. Vasc. Biol. ; 17: 1171-1177.
William E. Connor; P. Barton Duell; Ron Kean; Yingming Wang (2007) The Prime Role of HDL to Transport Lutein into the Retina: Evidence from HDL-Deficient WHAM Chicks Having a Mutant ABCA1 Transporter. Investigative Ophthalmology & Visual Science. vol. 48, 4226-4231.
Pan M, Cederbaum AI, Zhang YL, Ginsberg HN, Williams KJ, Fisher EA. (2004) Lipid peroxidation and oxidant stress regulate hepatic apolipoprotein B degradation and VLDL production. J Clin Invest.; 113: 1277-1287.
Esterbauer H, Schaur RJ, Zollner H. (1991) Chemistry and biochemistry of 4-hydroxynonenal, malonaldehyde and related aldehydes. Free Radic Biol Med, 11 : 81-128.
Shukla I, Azmi L, Gupta SS, Upreti DK, Rao CV. (2018) Melioration of anti-hepatotoxic effect by Lichen rangiferinus against alcohol induced liver damage in rats. J Ayurveda Integr Med. Jan. 29, 2018. pii: S0975-9476(I7)30047-5.
Patil, R.H., Prakash, K. and Maheshwari, V.L. (2011) Hypolipidemic effect of *Terminalia aijuna* (L.) in experimentally induced hypercholesteremic rats. Acta Biol. Szeged. 55(2), 289-293.

SYNERGISTIC HEPATOPROTECTIVE COMPOSITION

FIELD OF INVENTION

The present invention relates to a synergistic hepatoprotective composition and in particular to a synergistic hepatoprotective composition having a novel combination of the phytochemicals namely curcuminoids and carotenoids such as lutein. The synergistic hepatoprotective composition is effective in promoting health more particularly in protecting normal liver function. Also provided is a novel process for manufacturing such a composition and its use in foods, beverages including alcoholic beverages and as nutraceuticals, dietary supplements and pharmaceuticals.

BACKGROUND OF THE INVENTION

Phytochemicals are biologically active compounds present in plants used for food and medicine. Phytochemicals such as curcuminoids and carotenoids are known for their health promoting properties.

Turmeric (Curcuma longa) is a member of the ginger family (Zingiberaceae), which is a popular Indian spice and is extensively cultivated for its rhizomes. The curcuminoids are polyphenolic compounds in turmeric rhizomes and are responsible for the yellow color of turmeric. A great variety of pharmacological activities of Turmeric have also been reported. Curcumin is the principal curcuminoid of Turmeric. The other two curcuminoids are demethoxycurcumin and bis-demethoxycurcumin. Curcumin is one of the major components of Turmeric being responsible for its various biological actions. The biological effects of Curcumin range from antioxidant, anti-inflammatory to inhibition of angiogenesis and is also shown to possess specific antitumoral activity. Curcumin can bind with heavy metals such as cadmium and lead, thereby reducing the toxicity of these heavy metals. This property of Curcumin explains its protective action to the brain. Turmeric has been found to have a hepatoprotective characteristic similar to silymarin. Turmeric's hepatoprotective effect is mainly a result of its antioxidant properties, as well as its ability to decrease the formation of pro-inflammatory cytokines (1).

Lutein belongs to the large class of plant pigments generally seen with its isomer zeaxanthin and traces of other carotenes like beta-carotene and cryptoxanthin together referred to as Carotenoids. Its presence in human tissues is due entirely to ingestion of plant sources; it is not synthesized by animal tissues. Lutein is present in a wide variety of fruits and vegetables (2) and imparts a yellow color to the plants it is found in, such as corn. Its concentration is particularly high in leafy green vegetables such as spinach, collards and kale (2). It is also present in some animal products such as egg yolks (3) due to plant products eaten by animals. Various studies suggest that lutein may reduce risk of developing the two most common eye diseases in older people, i.e., cataract and macular degeneration. Oxidative stress is high in the eye due to the intense light exposure and the high rate of oxidative metabolism in the retina. The antioxidant properties of lutein may reduce the degree to which oxidative damage promotes these diseases or may minimize the damage due to oxidative stress by limiting the degree to which oxygen penetrates membranes (4,5). Further, associations have been found between individuals in the highest serum or dietary lutein levels and lower rates of coronary heart disease (6) or stroke (7). In two epidemiological studies, individuals with the highest serum levels of lutein plus zeaxanthin had a significantly reduced risk of coronary heart disease as measured by carotid intima thickness (8,9). Lutein and zeaxanthin are largely transported in plasma by high-density lipoprotein (HDL) (10).

The liver is a vital organ that plays a significant role in metabolism and detoxification of various endogenous and exogenous harmful substances. The major causes of liver diseases are toxic chemicals, excess consumption of alcohol, infections and autoimmune disorder. It is the liver where structural alteration of drugs takes place, resulting in biologically active or inactive metabolites and some of these are toxic. Thus, liver is a vulnerable target of injury from various chemicals and drugs.

Oxidative stress has been considered as a major contributor to initiation and progress of liver injury. Various risk factors such as alcohol and drugs are known to induce oxidative stress which in turn may lead to chronic disease such as Fatty liver disease. Fatty liver disease encompasses both alcoholic liver disease (ALD) and non-alcoholic fatty liver disease (NAFLD). Growing evidence suggests a vital role of oxidative stress caused by the generation of Reactive Oxygen Species (ROS) in the progression of ALD and NAFLD. Oxidative stress refers to an imbalance between the generation of ROS and oxidants and the countering activity of antioxidants (11). Over generation of ROS exerts deleterious effects in cell functions, ultimately contributing to fatty liver disease. In mitochondria, increased ROS production can cause mtDNA depletion, attack biomolecules (i.e. proteins, carbohydrates and lipids), and damage the mitochondrial membrane. It is worth noting that mitochondria have a substantial concentration of phospholipids containing polyunsaturated fatty acids (PUFAs). The PUFAs are more prone to oxidative damage, because of the double bonds in their chemical structure, which lead to lipid peroxidation. PUFA peroxidation enhances post-endoplasmic reticulum presecretory proteolysis of ApoB, thereby reducing VLDL secretion (12); this may further contribute to triglyceride (TG) accumulation in the liver. Moreover, aldehydes formed through PUFA peroxidation impair cellular homeostasis (13), because these molecules affect nucleotide and protein synthesis, reduce hepatic glutathione content and increase production of the proinflammatory cytokine TNF-α. These effects lead to hepatocyte death and necrosis, inflammation, and liver fibrosis.

Liver is the primary site for alcohol metabolism. Liver damage or liver toxicity occurs through several interrelated pathways. The primary pathway for the ethanol metabolism is dehydrogenase system. Alcohol dehydrogenase (ADH) and acetaldehyde dehydrogenase (ALDH) cause the reduction of nicotinamide adenine dinucleotide (NAD) to NADH (reduced form of NAD). The altered ratio of NAD/NADH promotes fatty liver through the inhibition of gluconeogenesis and fatty acid oxidation (14). Chronic alcohol exposure also activates hepatic macrophages, which then produce tumor necrosis factor-alpha (TNF-α) (15). TNF-α induces mitochondria to increase the production of reactive oxygen species (ROS). This oxidative stress promotes hepatocyte necrosis and apoptosis.

Further, as discussed above, Curcuminoids and Lutein are proven antioxidants and are helpful in preventing diseases caused due to oxidative stress. Therefore, it would be beneficial to prepare a composition comprising curcuminoids and lutein that will have potential beneficial effects on liver heath by protecting liver from any oxidative damages including damages caused by peroxidised poly unsaturated fatty acids.

It is therefore an objective of the present invention to provide a synergistic hepatoprotective composition comprising curcuminoids and lutein that exhibits synergistic effects of both the constituents at very low dosages and at the same time has high bioavailability thereby effectively promoting liver health.

SUMMARY OF INVENTION

The present invention relates to a synergistic hepatoprotective composition and in particular to a synergistic hepatoprotective composition having a novel combination of the phytochemicals namely curcuminoids and carotenoids such as lutein. The synergistic hepatoprotective composition is effective in promoting health more particularly in protecting normal liver health. Also provided is a novel process for manufacturing such a composition and its use in foods, beverages including alcoholic beverages and as nutraceutical products, dietary supplements and pharmaceuticals.

According to an embodiment of the invention there is provided a synergistic hepatoprotective composition comprising Curcuminoids and lutein.

According to an embodiment of the invention the synergistic hepatoprotective composition comprises of Curcuminoids and lutein wherein curcuminoids and lutein are present in a ratio in the range of 2:1: to 6:1.

According to another embodiment of the invention the ratio of Curcuminoids and lutein is in the range of 4:1 to 6:1 in the synergistic hepatoprotective composition.

According to another embodiment of the invention the synergistic hepatoprotective composition is effective in protecting the liver against liver damage or liver toxicity by attenuating formation of ROS, balancing the NADH/NAD ratios, down regulating the Inflammation pathway and controlling fatty liver formation.

According to another embodiment of the invention the synergistic hepatoprotective composition is effective in protecting the liver against liver damage or liver toxicity, which may be caused by various factors such as unhealthy dietary patterns, intake of high amounts of alcohol, intake of foods containing high amounts of peroxidized Polyunsaturated fatty acid (PUFA) content or due to consumption of certain drugs. Further, the hepatoprotective composition of the present invention is also effective in protecting liver against non-alcoholic fatty liver disease caused by unhealthy dietary patterns.

According to another embodiment of the invention the synergistic hepatoprotective composition is effective in protecting the liver against liver toxicity by way of suppressing the oxidative stress injury in the cells.

According to another embodiment of the invention the synergistic hepatoprotective composition is effective in protecting the liver against liver peroxidation as has been investigated through in vitro as well as in vivo studies by the inventors to study the efficacy of the synergistic hepatoprotective composition.

According to yet another embodiment of the invention the synergistic hepatoprotective composition is effective in normalizing and maintaining the lipid profile. Also, it is effective in maintaining healthy cholesterol levels and a healthy LDL/HDL ratio.

According to yet another embodiment of the invention the synergistic hepatoprotective composition is effective in protecting the liver against ethanol induced toxicity possibly through lipid lowering and hepatoprotective activity.

According to another embodiment of the invention the synergistic hepatoprotective composition may be taken/ingested on a regular basis as supplement or before, during or after intake of fatty foods, drugs and/or alcohol.

According to another embodiment of the invention there is provided a novel process for manufacturing the synergistic hepatoprotective composition comprising Curcuminoids and lutein wherein the process comprises:
  a) mixing the curcuminoids and lutein in predetermined ratios to form a dry blend; the particle size of the unprocessed dry blend may lie in the range of $D_{50}$-20 µm to 50 µm and $D_{90}$-100 µm to 200 µm;
  b) adding suitable emulsifier and maltodextrin to the dry blend;
  c) adding purified water to the dry blend to make a suspension;
  d) subjecting the suspension to pass through liquid colloidal mill to form a uniform suspension;
  e) subjecting the suspension to further processing such as passing through a homogenizer or a high shear particle wet mill to produce a micronized emulsion;
  f) further agitating the micronized emulsion for 8-12 hrs at a speed of 25 rpm to bring the mass temperature to a temperature of 25° C.-40° C., preferably 25° C.-30° C.);
  g) subjecting the micronized emulsion to further processing such as concentration and/or drying to obtain the synergistic hepatoprotective composition.

The process further comprises passing the dried synergistic hepatoprotective composition through a suitable particle sieve to obtain a uniform finished product. The particle size of such a processed composition may lie in the range of $D_{50}$-0.36 µm to 5 µm and $D_{90}$ in the range of 0.60 µm to 10 µm. Such a particle size reduction helps the synergistic hepatoprotective composition to have high bioavailability.

According to an embodiment of the invention the predetermined ratio of the curcuminoids and lutein may be in the range of 2:1 to 6:1.

According to another embodiment of the invention the predetermined ratio of the curcuminoids and lutein may be in the range of 4:1 to 6:1.

According to another embodiment of the invention the synergistic hepatoprotective composition may be added to a food and/or beverage product or formulated into a dietary supplement.

According to another embodiment of the invention the synergistic hepatoprotective composition may be used as a dietary/nutritional supplement or as a therapeutic/health ingredient in various food and beverage products. Some examples of food and beverages where the synergistic hepatoprotective composition may be used as a health ingredient include but are not limited to tea, infusions, fruit juices, drinks, milk and milk products, cereal based products, alcoholic beverages and processed foods etc.

According to another embodiment of the invention the synergistic hepatoprotective composition may also be formulated into suitable dosage forms selected from a group comprising of powder, paste, tablets, syrups and/or capsules etc.

According to another embodiment of the invention the Curcuminoids and Lutein in the synergistic hepatoprotective composition are present at much lower amounts than the recommended daily requirement and exhibit a synergistic activity.

The above and other features and aspects of the present invention are more clearly described in the complete specification.

BRIEF DESCRIPTION OF DRAWINGS

The invention can be described in the terms of the following figures where.

DETAILED DESCRIPTION OF THE INVENTION

Figure 1:
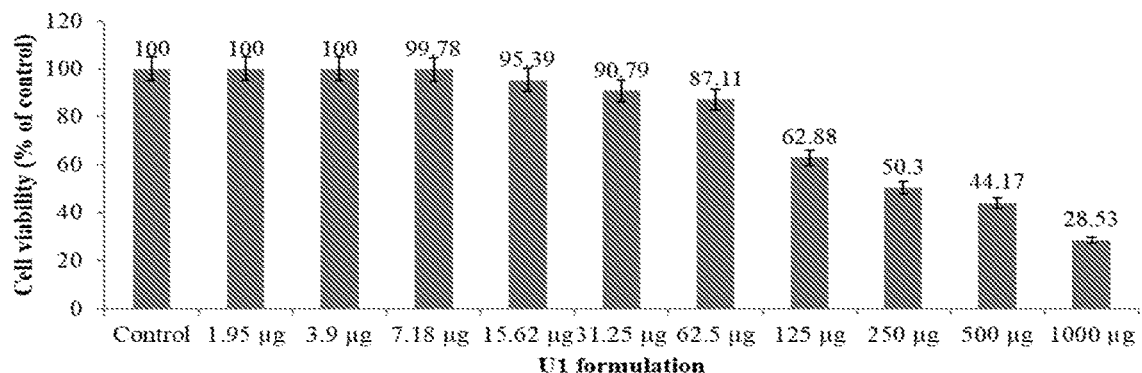
-FIG. 1(a) illustrates cytotoxicity effects of different concentrations of the unprocessed Curcuminoids (U1) in HepG2 cells.
FIG. 1(b) illustrates cytotoxicity effects of different concentrations of the unprocessed Lutein (U2) in HepG2 cells.
FIG. 1(c) illustrates cytotoxicity effects of different concentrations of the unprocessed synergistic hepatoprotective composition (U3) in HepG2 cells.
FIG. 1(d) illustrates cytotoxicity effects of different concentrations of the processed Curcuminoids (P1) in HepG2 cells.
FIG. 1(e) illustrates cytotoxicity effects of different concentrations of the processed Lutein (P2) in HepG2 cells.
FIG. 1(f) illustrates cytotoxicity effects of different concentrations of the processed synergistic hepatoprotective composition (P3) in HepG2 cells.
Figure 1B:
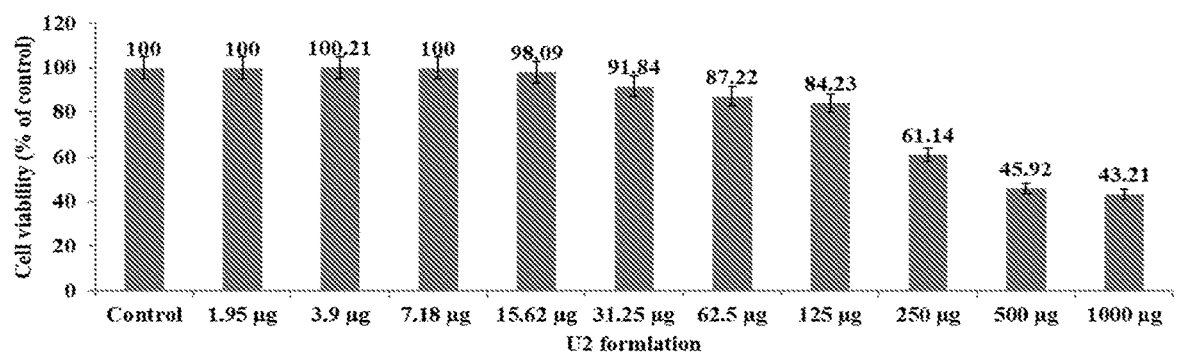
Figure 1:
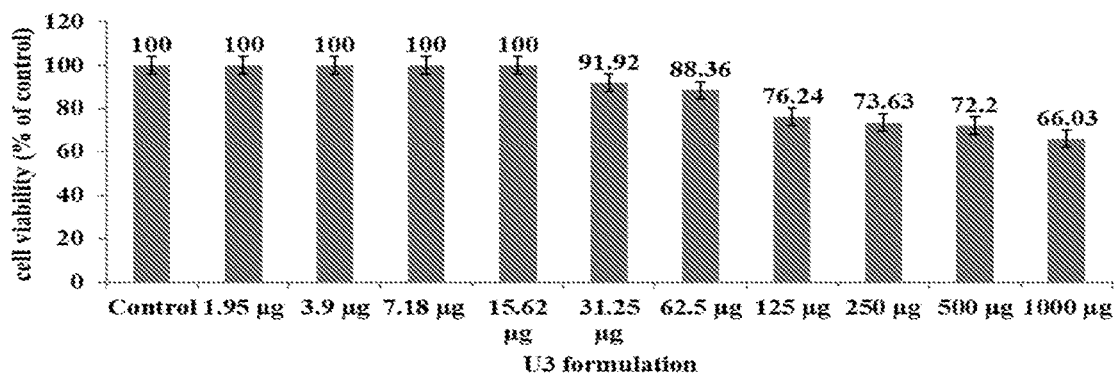
Figure 1D:
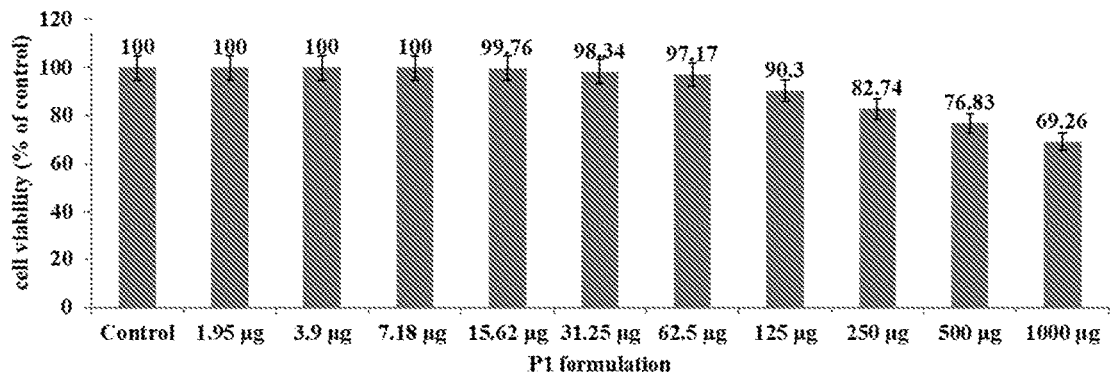
Figure 1E:
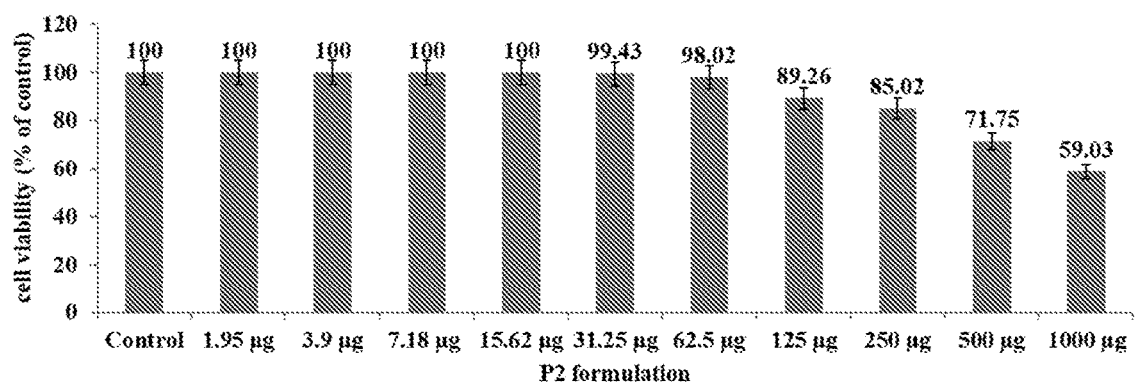
Figure 1:
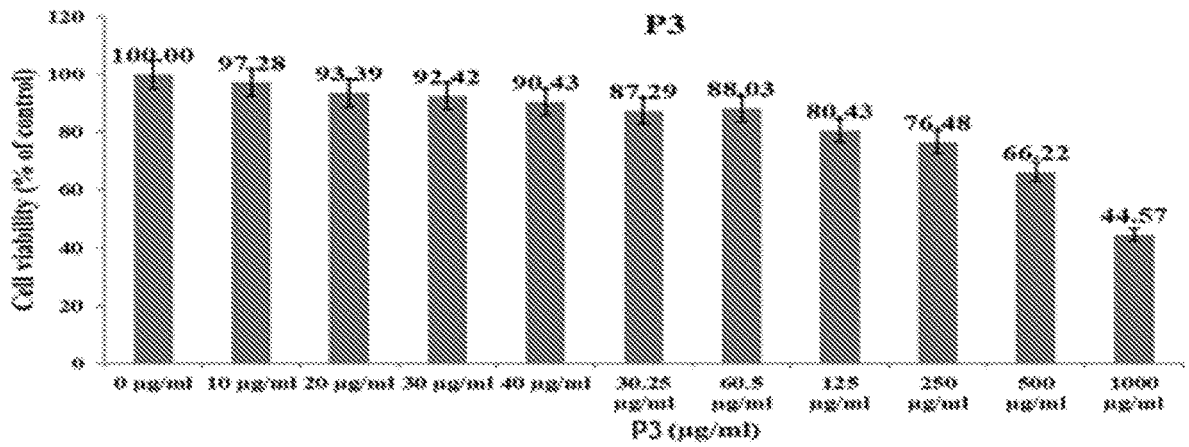

Discussed below are some representative embodiments of the present invention. The invention in its broader aspects is not limited to the specific details and representative methods. The illustrative examples are described in this section in connection with the embodiments and methods provided. The invention according to its various aspects is particularly pointed out and distinctly claimed in the attached claims read in view of this specification.

It is to be noted that, as used in the specification and the appended claims, the singular forms "a," "an," and "the" include plural referents unless the context clearly dictates otherwise. Thus, for example, reference to a composition containing "a compound" includes a mixture of two or more compounds. It should also be noted that the term "or" is generally employed in its sense including "and/or" unless the content clearly dictates otherwise.

The expression of various quantities in terms of "%" means the percentage by weight of the total solution or composition unless otherwise specified.

All cited references are incorporated herein by reference in their entireties. Citation of any reference is not an admission regarding any determination as to its availability as prior art to the claimed invention.

Technical and scientific terms used herein have the meaning commonly understood by one of skill in the art to which the present invention pertains, unless otherwise defined.

Reference is made herein to various methodologies and materials known to those of skill in the art.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The present invention, in its product and process aspects, is described in detail as follows.

The present invention relates to a synergistic hepatoprotective composition and in particular to a synergistic hepatoprotective composition having a novel combination of the phytochemicals namely curcuminoids and carotenoids such as lutein. The synergistic hepatoprotective composition is effective in promoting health more particularly in protecting liver function. Also provided is a method for manufacturing such a composition and its use in foods, beverages including alcoholic beverages and nutraceutical products and/or as a dietary supplement.

According to an embodiment of the invention there is provided a synergistic hepatoprotective composition comprising Curcuminoids and lutein.

According to an embodiment of the invention the synergistic hepatoprotective composition comprises Curcuminoids and lutein in a ratio in the range of 2:1: to 6:1.

According to an embodiment of the invention the ratio of the Curcuminoids and lutein is in the range of 4:1 to 6:1 in the synergistic hepatoprotective composition.

According to an embodiment of the invention the curcuminoids and lutein are present in their purified form in the synergistic hepatoprotective composition. The purity of the curcuminoids may be in the range of 80-95% and the purity of lutein may be in the range of 70-85%.

According to an embodiment of the invention the Curcuminoids may be obtained/extracted and purified from the plant *Curcuma longa* and the lutein may be obtained/extracted and purified from the Marigold plant *Tagetes erecta* or any other suitable plant source.

According to another embodiment of the invention the synergistic hepatoprotective composition is effective in protecting the liver against liver damage or liver toxicity. Some of the causative factors of liver damage or liver toxicity could be unhealthy dietary patterns, intake of high amounts of alcohol, consumption of certain drugs or consumption of foods containing high amounts of peroxidised polyunsaturated fatty acid (PUFA) in the diet. Further, the synergistic hepatoprotective composition of the present invention is also effective in protecting liver against non-alcoholic fatty liver disease caused by unhealthy dietary patterns.

According to another embodiment of the invention the synergistic hepatoprotective composition is effective in protecting the liver against liver toxicity by a suppressing action on the oxidative stress injury in the cells.

According to another embodiment of the invention the synergistic hepatoprotective composition is effective in protecting the liver against oxidative stress injury in the liver cells which may be caused by various factors such as alcohol intake, drug intake or unhealthy dietary patterns including intake of high amounts of peroxidised PUFA in the diet etc..

According to another embodiment of the invention the synergistic hepatoprotective composition is effective in protecting the liver against liver peroxidation induced by factors such as alcohol intake, drug intake or unhealthy dietary patterns including intake of high amounts of peroxidised PUFA in the diet etc..

According to another embodiment of the invention the synergistic hepatoprotective composition is effective in protecting the liver against liver peroxidation by decreasing the production of Thiobarbituric acid reactive species (TBARS) Malondialdehyde (MDA) in the affected cells as is exhibited in the in-vitro studies.

According to another embodiment of the invention the synergistic hepatoprotective composition is effective in protecting the liver against liver toxicity by increasing the levels of non-enzymatic antioxidants Glutathione reductase (GSH) and superoxide dismutase (SOD) in the affected cells. The decrease in non-enzymatic antioxidants may be caused by various factors such as alcohol intake, drug intake or unhealthy dietary patterns including intake of high amounts of peroxidised PUFA in the diet etc..

According to another embodiment of the invention the synergistic hepatoprotective composition is effective in protecting the liver against liver damage or liver toxicity by attenuating formation of ROS, balancing the NADH/NAD ratios, down regulating the Inflammation pathway and controlling fatty liver formation.

According to yet another embodiment of the invention the synergistic hepatoprotective composition of the present invention is effective in protecting the liver against liver toxicity by preventing reactive oxygen species (ROS) generation in the affected cells thereby subsequently attenuating the further degeneration pathway of inflammation in the affected cells. The increased ROS generation may be caused by various factors such as alcohol intake, drug intake or unhealthy dietary patterns including intake of high amounts of peroxidised PUFA in the diet etc.. The synergistic hepatoprotective composition also effectively protects the liver against liver toxicity induced by factors such as alcohol, drugs and unhealthy dietary patterns by preventing the depolarization of mitochondrial membrane of cells in the affected cells.

In an embodiment of the invention the synergistic hepatoprotective composition of the present invention effectively protects the liver against liver toxicity induced by factors such as alcohol, drugs and unhealthy dietary patterns, by preventing the nuclear apoptosis and nuclear fragmentation of cells in the affected cells as is established by in-vitro studies.

In yet another embodiment of the invention the synergistic hepatoprotective composition of the present invention is effective in suppressing the increased levels of the serum enzymes namely Alanine aminotransferase (ALT), Aspartate aminotransferase (AST), Alcohol Dehydrogenase (ADH) and Gammaglutamyl transferase (GGT) as is established by pre-clinical studies.

According to another embodiment of the invention the synergistic hepatoprotective composition is effective in protecting the liver against liver peroxidation as has been investigated through in vitro as well as in vivo studies by the inventors to study the efficacy of the synergistic hepatoprotective composition.

According to yet another embodiment of the invention the synergistic hepatoprotective composition is effective in normalizing and maintaining the lipid profile. Also, it is effective in maintaining healthy cholesterol levels and a healthy LDL/HDL ratio.

According to yet another embodiment of the invention the synergistic hepatoprotective composition is effective in protecting the liver against liver toxicity induced by factors such as alcohol, drugs and unhealthy dietary patterns possibly through lipid lowering and hepatoprotective activity.

In accordance to another embodiment of the invention the Curcuminoids and Lutein are obtained from natural sources, which are known to be free of side effects.

According to another embodiment of the invention the synergistic hepatoprotective composition may be taken/ingested on a regular basis as supplement or before, during or after intake of fatty foods, drugs and/or alcohol.

The present invention also provides a process for manufacturing a synergistic hepatoprotective composition comprising lutein and Curcuminoids wherein the process comprises the following steps:

a) mixing the curcuminoids and lutein in predetermined ratios to form a dry blend; the particle size of the unprocessed dry blend may lie in the range of $D_{50}$-20 µm to 50 µm and $D_{90}$-100 µm to 200 µm;
b) adding a suitable emulsifier and maltodextrin to the dry blend;
c) adding purified water to the dry blend to make a suspension;
d) subjecting the suspension to pass through liquid colloidal mill to form a uniform suspension;
e) subjecting the suspension to further processing such as passing through a homogenizer or a high shear particle wet mill to produce a micronized emulsion;
f) further agitating the micronized emulsion for 8-12 hrs at a speed of 25 rpm to bring the mass temperature to a temperature of 25° C.-40° C., preferably 25° C.-30° C.;
g) subjecting the micronized emulsion to further processing such as concentration and/or drying to obtain the synergistic hepatoprotective composition.

In the above process, the curcuminoids taken for preparation of the synergistic hepatoprotective composition may be of a purity of 80-95% and the purity of lutein may be in the range of 70-85%. Further, some examples of the emulsifiers that may be used are but not limited to modified starch, Gum ghatti, Gum Arabic, Gum Acacia, Methyl cellulose and sucrose fatty acid esters etc.

The process further comprises passing the dried hepatoprotective composition through a suitable particle sieve to obtain a uniform finished product. The particle size of the processed composition may lie in the range of $D_{50}$-0.36 µm to 5 µm and $D_{90}$ in the range of 0.60 µm to 10 µm. Such a particle size reduction helps the synergistic hepatoprotective composition to have high bioavailability.

According to an embodiment of the invention the predetermined ratio of the curcuminoids and lutein may be in the range of 2:1 to 6:1.

According to another embodiment of the invention the predetermined ratio of the curcuminoids and lutein may be in the range of 4:1 to 6:1.

According to another embodiment of the invention the synergistic hepatoprotective composition may be added to the food and/or beverage product, formulated into a dietary supplement, nutraceuticals and/or pharmaceuticals.

According to another embodiment of the invention the synergistic hepatoprotective composition may be used as a nutraceutical, pharmaceutical, dietary/nutritional supplement or as a therapeutic/health ingredient in various food and beverage products. Some examples of food and beverages where the synergistic hepatoprotective composition may be used as a health ingredient include but are not limited to tea, infusions, fruit juices, drinks, milk and milk products, cereal based products, alcoholic beverages and processed foods etc.

According to another embodiment of the invention the synergistic hepatoprotective composition may also be formulated into suitable dosage forms selected from a group comprising of powder, paste, tablets, syrups, infusions and or capsules etc.

According to another embodiment of the invention the Curcuminoids and Lutein of the synergistic hepatoprotective composition are present at much lower amounts than the recommended daily requirement and exhibit a synergistic activity.

In an embodiment of the invention the synergistic hepatoprotective composition may also be added to any alcoholic beverage to counter the ill-effects of alcohol while being consumed by the person.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

In this example, representative synergistic hepatoprotective compositions of the present invention comprising Curcuminoids and Lutein in different ratios by weight are described. Table 1 shows the components and their amounts used in the synergistic hepatoprotective composition having Curcuminoids and Lutein in different ratios.

TABLE 1

Components used for preparing the synergistic hepatoprotective compositions of present invention

| Ratio of Curcumin to Lutein in the Composition | Curcuminoids (g) | Lutein (g) | Emulsifier (g) | Maltodextrin (g) |
|---|---|---|---|---|
| 2:1 | 32 | 18.75 | 39.25 | 10 |
| 2:1 | 26.32 | 15.63 | 48.05 | 10 |
| 3:1 | 32 | 12.5 | 45.5 | 10 |
| 3:1 | 10.53 | 4.16 | 75.31 | 10 |
| 4:1 | 32 | 9.38 | 48.62 | 10 |
| 4:1 | 26.32 | 7.82 | 55.86 | 10 |
| 6:1 | 32 | 6.25 | 51.75 | 10 |
| 6:1 | 26.32 | 5.21 | 58.47 | 10 |

Example 2

The synergistic hepatoprotective compositions as elaborated in Example 1 was manufactured by the process as described below:

Curcuminoids (purity 95%) and Lutein (purity 80%) were mixed together with modified starch emulsifier and maltodextrin in the given quantities to prepare a dry blend (100 g). The particle size of the dry blend was $D_{50}$-20 µm and $D_{90}$-100 µm. This dry blend was then reconstituted with 333.4 ml of RO purified water to make a suspension and further agitated till there were no lumps present in the suspension. The suspension was then pre-emulsified in a liquid colloidal mill or liquid wet mill to form a uniform emulsion. The pre-emulsion thus obtained was passed through high pressure homogenizer/high shear particle wet mill to produce submicron size emulsion droplets. The micronized emulsion was further agitated for 8-12 hrs at the speed to 25 rpm to bring the mass temperature to 25° C.-40° C., preferably 25° C.-30° C. This micronized emulsion was further spray dried with chamber temperature being not more than 110° C. The spray dried coarse powder was then collected and subjected to dry milling using either micro pulveriser or air assisted high shear dry milling. The milled particles were collected and passed though suitable particle sieve and blend to get the final product. The particle size of the final powder was $D_{50}$-0.360 µm and $D_{90}$-0.60 µm.

Example 3

The synergistic hepatoprotective compositions as elaborated in Example 1 was manufactured by the process as described below:

Curcuminoids (purity 90%) and Lutein (purity 75%) were mixed together with modified starch emulsifier and maltodextrin in the given quantities to prepare a dry blend (100 g). The particle size of the dry blend was $D_{50}$-40 µm and $D_{90}$-155 µm. This dry blend was then reconstituted with 333.4 ml of RO purified water to make a suspension and further agitated till there were no lumps present in the suspension. The suspension was then pre-emulsified in a liquid colloidal mill or liquid wet mill to form a uniform emulsion. The pre-emulsion thus obtained was passed through high pressure homogenizer/high shear particle wet mill to produce submicron size emulsion droplets. The micronized emulsion was further agitated for 8-12 hrs at the speed to 25 rpm to bring the mass temperature to 25° C.-40° C., preferably 25° C.-30° C. This micronized emulsion was further spray dried with chamber temperature being not more than 110° C. The spray dried coarse powder was then collected and subjected to dry milling using either micro pulveriser or air assisted high shear dry milling. The milled particles were collected and passed though suitable particle sieve and blend to get the final product. The particle size of the final powder was $D_{50}$-2.76 µm and $D_{90}$-5.44 µm.

Example 4

The synergistic hepatoprotective composition as elaborated in Example 1 was manufactured by the process as described below:

Curcuminoids (purity 85%) and Lutein (purity 70%) were mixed together with modified starch emulsifier and maltodextrin in the given quantities to prepare a dry blend (100 g). The particle size of the dry blend was $D_{50}$-50 µm and $D_{90}$-200 µm. This dry blend was then reconstituted with 333.4 ml of RO purified water to make a suspension and further agitated till there were no lumps present in the suspension. The suspension was then pre-emulsified in a liquid colloidal mill or liquid wet mill to form a uniform emulsion. The pre-emulsion thus obtained was passed through high pressure homogenizer/high shear particle wet mill to produce submicron size emulsion droplets. The micronized emulsion was further agitated for 8-12 hrs at the speed to 25 rpm to bring the mass temperature to 25° C.-40° C., preferably 25° C.-30° C. This micronized emulsion was further spray dried with chamber temperature being not more than 110° C. The spray dried coarse powder was then collected and subjected to dry milling using either micro pulveriser or air assisted high shear dry milling. The milled particles were collected and passed though suitable particle sieve and blend to get the final product. The particle size of the final powder was $D_{50}$-5 µm and $D_{90}$-10 µm.

Example 5

In-Vitro Studies to Assess the Hepatoprotective Effect of the Synergistic Hepatoprotective Composition on Ethanol-Induced and Drug-Induced Hepatotoxicity Objective:

The main objective of the study was to investigate the effect of the synergistic hepatoprotective composition of the present invention vs. silymarin on Ethanol and acetaminophen (APAP)-induced hepatotoxicity via suppressing oxidative stress injury in HepG2 cell line. As Silymarin is a widely used hepatoprotective agent, it was taken to compare the efficacy of the novel synergistic hepatoprotective composition of the present invention.

Cell Line and Culture Medium:

This work was carried out in human liver hepatocarcinoma (HepG2) cells. The HepG2 cells were obtained from National Centre for Cell Science, Pune, India. Cells were maintained in DMEM medium with 10% FBS, 1% glutamine, and 100 U penicillin-streptomycin at 37° C. in 5% $CO_2$ atmosphere. Stocks were maintained in T-75 $cm^2$ tissue culture flasks.

Experiments

Cytotoxicity Studies

The nontoxic concentrations of Unprocessed Curcuminoids (U1), unprocessed Lutein (UJ2), unprocessed synergistic hepatoprotective composition (U3) and processed Curcuminoids (P1), processed Lutein (P2) and Processed synergistic hepatoprotective composition (P3), Silymarin and its preventive effect against Ethanol and Acetaminophen (APAP)-induced cytotoxicity were assessed by MTT assay.

Preparation of Sample:
1. Unprocessed Curcuminoids (U1) sample was prepared by taking the purified curcuminoid and mixing it with the dry constituents namely emulsifier and maltodextrin in predetermined amounts.
2. Unprocessed Lutein (U2) sample was prepared by taking the purified lutein and mixing it with the dry constituents namely emulsifier and maltodextrin in predetermined amounts.
3. Unprocessed synergistic hepatoprotective composition (U3) sample was prepared by mixing the curcuminoids and lutein in a predetermined ratio and further dry blending with the emulsifier and maltodextrin in predetermined amounts.
3. Processed curcuminoids (P1) sample was prepared by taking the purified curcuminoid and mixing it with the dry constituents namely emulsifier and maltodextrin. This dry blend was then subjected to processing similar to the processing as described for the synergistic hepatoprotective composition in any of the above examples 2 to 4.
4. Processed lutein (P2) sample was prepared by taking the purified lutein and mixing it with the dry constituents namely emulsifier and maltodextrin. This dry blend was then subjected to processing similar to the processing as described for the synergistic hepatoprotective composition in any of the above examples 2 to 4.
5. Processed synergistic composition sample (P3) was prepared as described in any of the above examples 2 to 4.

HepG2 cells were collected and seeded in 96 well plates at density ($1\times10^5$ cells/well). To determine the toxicity of U1, U2, U3, P1, P2, P3 (1.95, 390, 7.81, 15.62, 31.25, 62.50, 125, 250, 500 and 1000 µg/ml) for 24 hours and MTT assay was performed. To assess the therapeutic efficacy of U1, U2, U3, P1, P2, P3 against ethanol and ethanol and APAP, cells were pre-treated with difference concentration of U1, U2, U3, P1, P2, P3 (3.90, 7.81, 15.62, 31.25, 62.50 and 125 µg/ml) and Silymarin (3.12-200 µg) 1 h before Ethanol (100 mM) and Acetaminophen (APAP) (20 mM) exposure. Then, 100 µl of MTT solution (5 mg/ml in PBS) was added and the incubation was extended for another 4 h. Then, 100 al of DMSO was added and absorbance was measured using multimode plate reader at 570 nm.

Lipid Peroxidation and Antioxidant Enzyme Activity Assay

Concentration of malondialdehyde (MDA), an index of lipid peroxidation, was determined based on thiobarbituric acid reactive species (TBARS) production, superoxide dismutase (SOD) activity and glutathione reductase (GSH) was measured according to the kit method (Himedia and Sigma). Samples were measured by the standard spectrophotometric methods.

Cells were incubated with Ethanol (100 mM) U1, U2, U3, P1, P2 and P3 and silymarin for 24 h. Total GSH content, activities of SOD and lipid peroxidations in hepatoprotective compositions were measured.

Cells were incubated with APAP (20 mM) and P3, silymarin for 24 h. Total GSH content, activities of SOD and lipid peroxidation in hepatoprotective compositions were measured.

Measurement of Intracellular ROS

ROS was measured using a non-fluorescent probe, 2,7-diacetyl dichlorofluorescein (DCFH-DH) that can penetrate into the intracellular matrix of cells, where it is oxidized by ROS to fluorescent dichlorofluorescein (DCF). Briefly, an aliquot of isolated cells ($8 \times 10^6$ cells/ml) were made up to a final volume of 2 ml in normal phosphate buffered saline (pH 7.4). 1 ml aliquot of cells was taken to which 1 µl DCFH-DA (1 mg/mL) was added and incubated at 37° C. for 30 min under dark condition. Images were taken on an epifluorescent microscope (Nikon, Eclipse TS100, Japan) with a digital camera (Nikon 4500 coolpix, Japan).

HepG2 cells were treated with 62.50 µg U1, U2, U3, P1, P2, P3 and 50 µg silymarin for 1 hours then treated with Ethanol 100 mM for 24 hours. Intracellular ROS accumulation was measured using the fluorescence probe DCF-DA.

Determination of Mitochondrial Membrane Potential

Reduced MMP is a sign of early apoptosis. In this study, difference in MMP was detected by fluorescent dye rhodamine 123 (Rh 123). HepG2 cells were cultured in 6-well plates ($1 \times 10^6$) and collected at the end of indicated treatment. After incubation with test compound and Ethanol or APAP for 24 hours, cells were incubated with Rh 123 (5 mmol/ml) for 15 minutes. Cells were then rinsed with PBS, fluorescence was observed under fluorescence microscope using blue filter (450-490 nm).

Dual Fluorescent and DAPI Staining for HepG2 Cells

HepG2 cells were grown in 35 mm cell culture dishes, treated with each candidate compounds P3 (62.50 g), Silymarin (50 g) and Ethanol 100 mM or APAP (20 mM) for 24 h, and washed with Dulbecco's phosphate buffered saline (DPBS). Morphological changes related to Ethanol or APAP-induced hepatotoxicity were detected using acridine orange/ethidium bromide (AO/EB) fluorescent staining. Ethidium bromide (100 mg/mL) and acridine orange (100 mg/mL) were mixed at 1:1 and DAPI 100 mg mL added to cells followed by fluorescent microscopy to evaluate morphological characteristics.

Results:

A. Cytotoxicity Effects of Unprocessed and Processed Ingredients and Synergistic Hepatoprotective Composition in HepG2 Cells FIGS. 1(a, b, c) show the cytotoxicity effects of different concentrations of the unprocessed ingredients and synergistic hepatoprotective composition in HepG2 cells. FIGS. 1(d, e and f) show the cytotoxicity effects of different concentrations of the processed ingredients and processed synergistic hepatoprotective composition in HepG2 cells.

Figure 2:
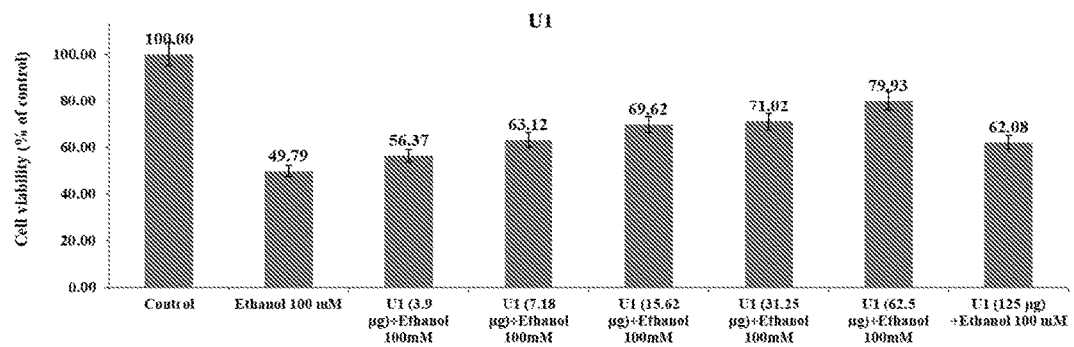
FIG. 2(a) illustrates cytotoxicity effects of different concentrations of the unprocessed Curcuminoids (U1) in ethanol induced HepG2 cells.
FIG. 2(b) illustrates cytotoxicity effects of different concentrations of the unprocessed Lutein (U2) in ethanol induced HepG2 cells.
FIG. 2(c) illustrates cytotoxicity effects of different concentrations of the unprocessed synergistic hepatoprotective composition (U3) in ethanol induced HepG2 cells.
FIG. 2(d) illustrates cytotoxicity effects of different concentrations of the processed Curcuminoids (P1) in ethanol induced HepG2 cells.
FIG. 2(e) illustrates cytotoxicity effects of different concentrations of the processed Lutein (P2) in ethanol induced HepG2 cells.
FIG. 2(f) illustrates cytotoxicity effects of different concentrations of the processed synergistic hepatoprotective composition (P3) in ethanol induced HepG2 cells.
Figure 2:
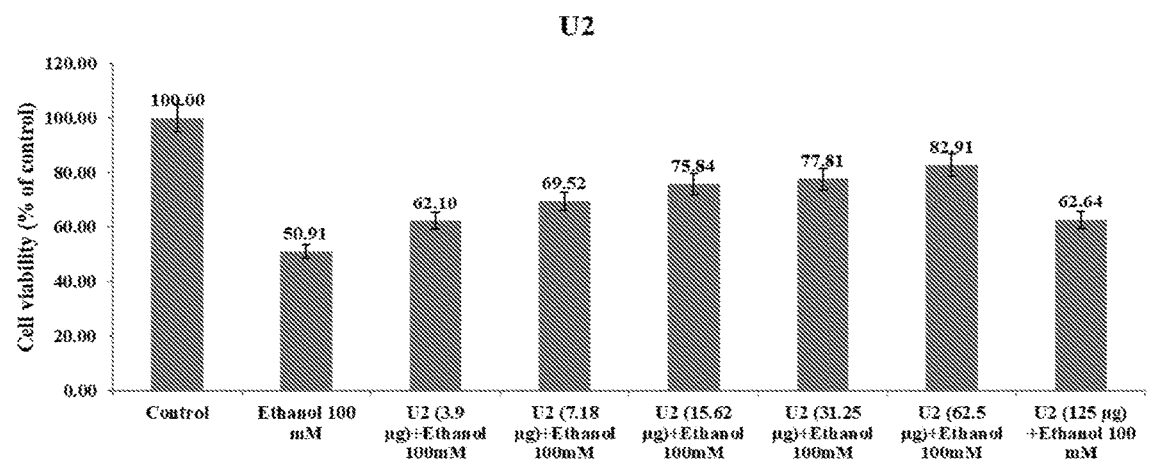
Figure 2:
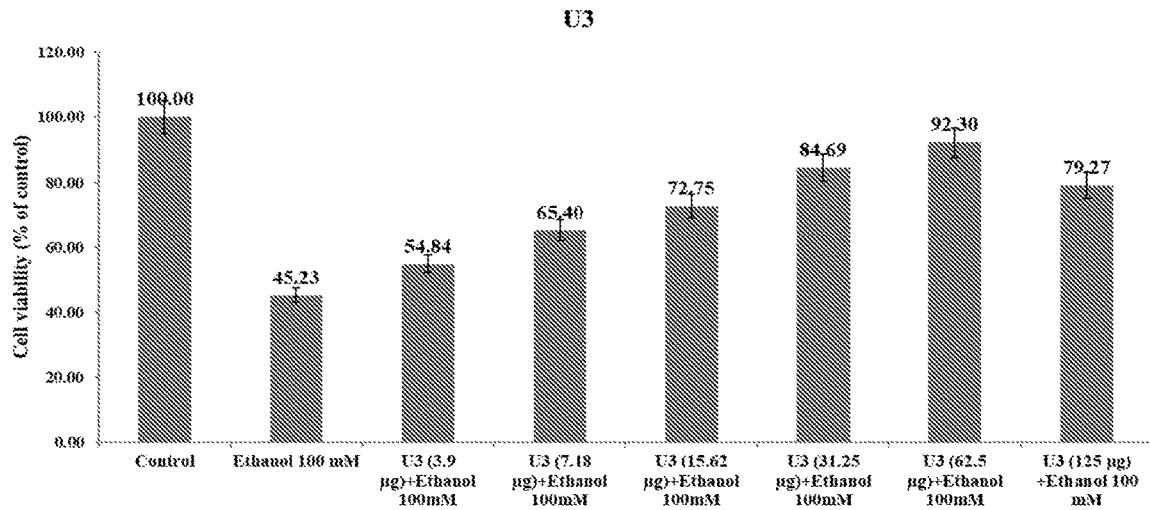
Figure 2:
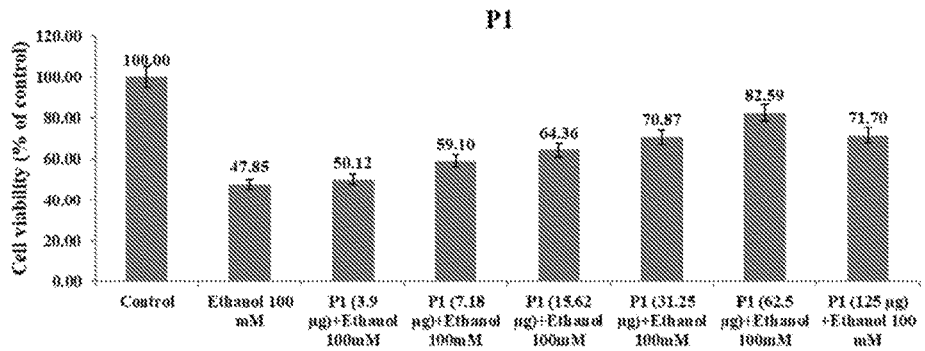
Figure 2:
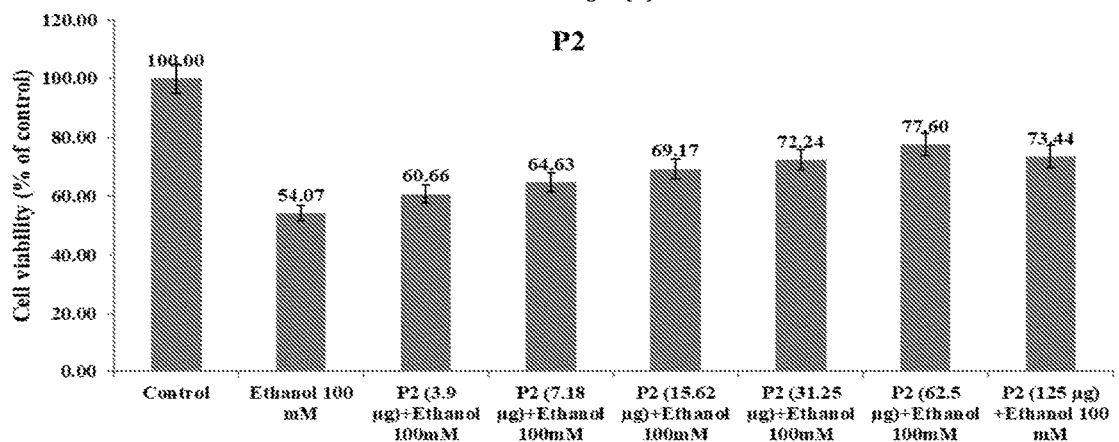
Figure 2:
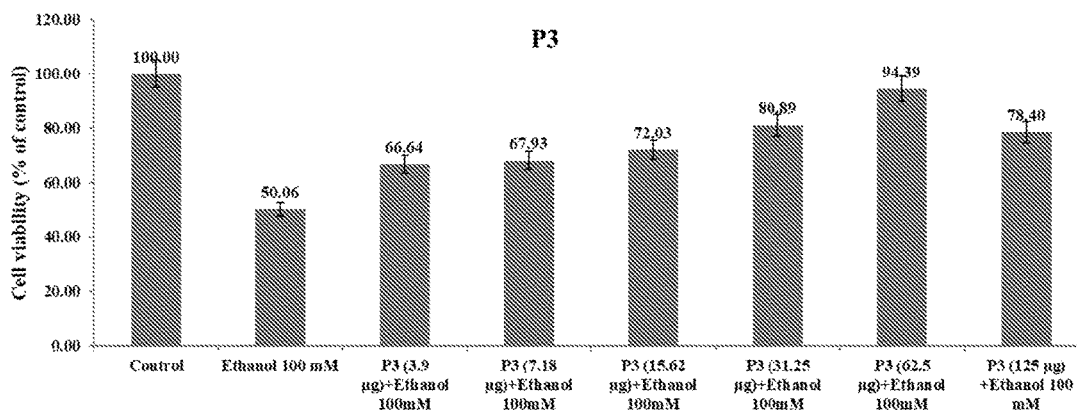

FIGS. 2(a, b, c) show the cytotoxicity effects of different concentrations of the processed ingredients and synergistic hepatoprotective composition in ethanol induced HepG2 cells. Whereas FIGS. 2(d, e, f) show the cytotoxicity effects of different concentrations of the processed ingredients and synergistic hepatoprotective composition in ethanol induced HepG2 cells.

The MTT assay exhibited that cell viability was not altered at low concentration 1.95-62.50 µg/ml in HepG2 cells. In addition of 3.9-62.50 µg/ml of U1, U2, U3, P1, P2, P3 led to significant increases in cell viability compared to ethanol. The maximal viability of cells was observed when exposed to 62.50 µg/ml (FIG. 2(a, b, c, d, e and f)).

Hence, 62.50 µg/ml concentrations of U1, U2, U3, P1, P2, P3 were chosen as an optimum protective concentration for all further studies.

Figure 3:
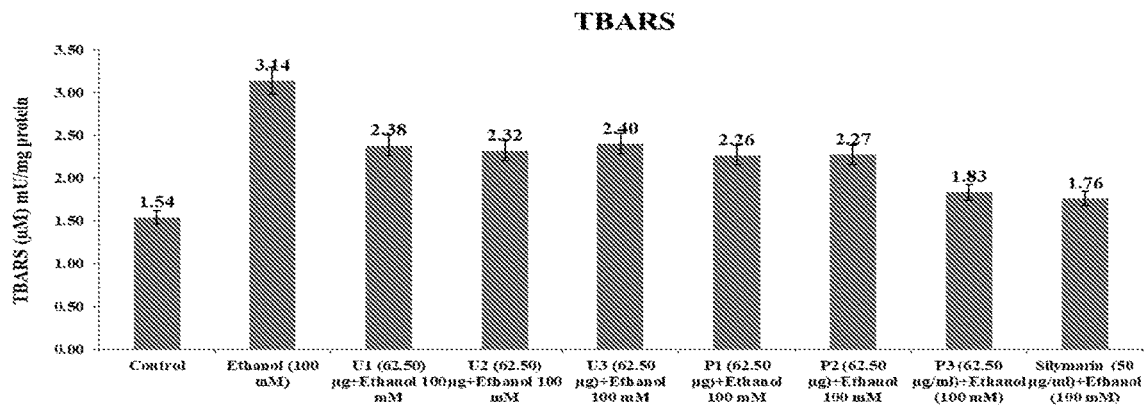
FIG. 3(a) illustrates hepatoprotective effects of the unprocessed and processed Synergistic Hepatoprotective composition on TBARS activity in ethanol induced HepG2 cells.
FIG. 3(b) illustrates hepatoprotective effects of the unprocessed and processed Synergistic Hepatoprotective composition on SOD activity in ethanol induced HepG2 cells.
FIG. 3(c) illustrates hepatoprotective effects of the unprocessed and processed Synergistic Hepatoprotective composition on GSH levels in ethanol induced HepG2 cells.
Figure 3:
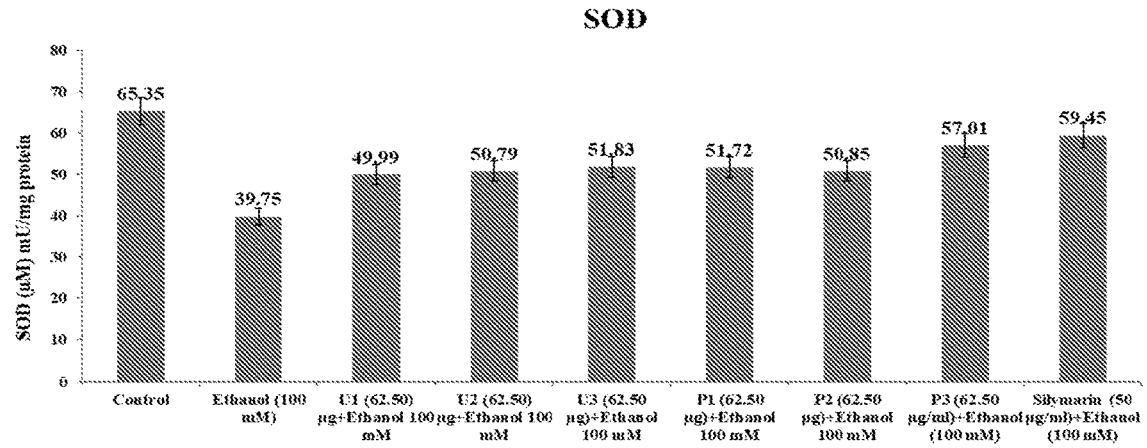
Figure 3:
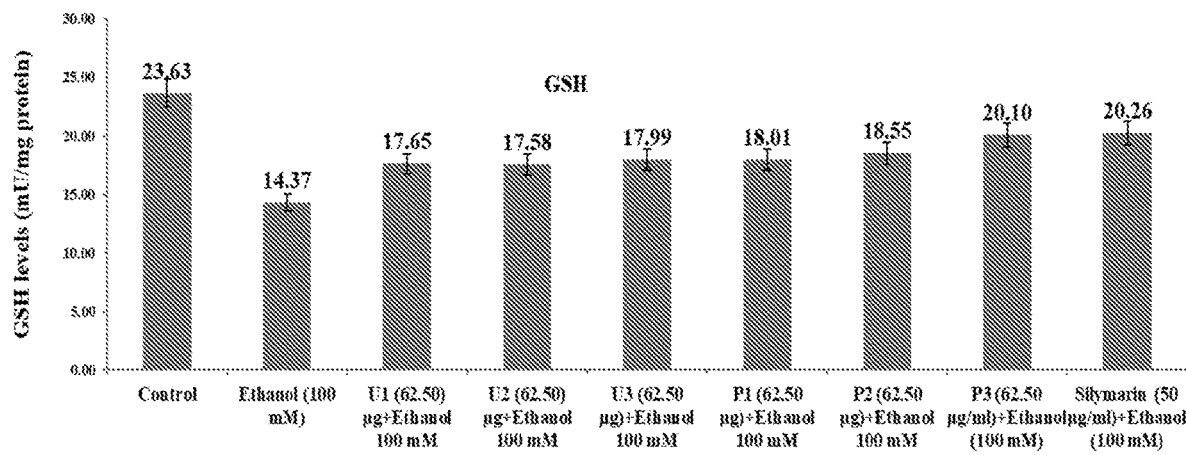

B. Hepatoprotective Effects of Unprocessed and Processed Ingredients and Synergistic Hepatoprotective Composition on Antioxidant Enzyme Activity in Ethanol-Induced HepG2 Cells The TBARS assay was performed to study U1, U2, U3, P1, P2, P3 and Silymarin capacity to alter the ethanol-induced lipid peroxidation in HepG2 cells (FIG. 3a). The results revealed higher TBARS formation in ethanol stimulation group compared to control cells. But the TBARS formation was decreased by treated cells respectively.

The effect of U1, U2, U3, P1, P2, P3 and Silymarin on ethanol-induced activities of SOD and GSH level is shown in FIGS. 3(b) and 3(c). Ethanol stimulation significantly reduced the levels of non-enzymatic antioxidant GSH and activities of SOD in HepG2 cells compared to control cells. Interestingly SOD and GSH was increased in U1, U2, U3, P1, P2, P3 as well as Silymarin treated cells compared to ethanol stimulation group.

Further, the effect of the processed synergistic hepatoprotective composition (P3) was comparable to that of Silymarin and the Control group. Furthermore, the effect shown by P3 were better than the effects shown by the unprocessed composition and that of the individual components Curcuminoids (U1, P1) and Lutein (U2, P2).

Hence, it could be inferred from these results that the processed form of the composition of the present invention (P3) exhibited a synergistic activity of the individual components viz. Curcuminoids and Lutein.

C. Cytotoxicity Effects of the Processed Synergistic Hepatoprotective Composition Vs. Silymarin in HepG2 Cells Treated with Acetaminophen (APAP)

Figure 4A:
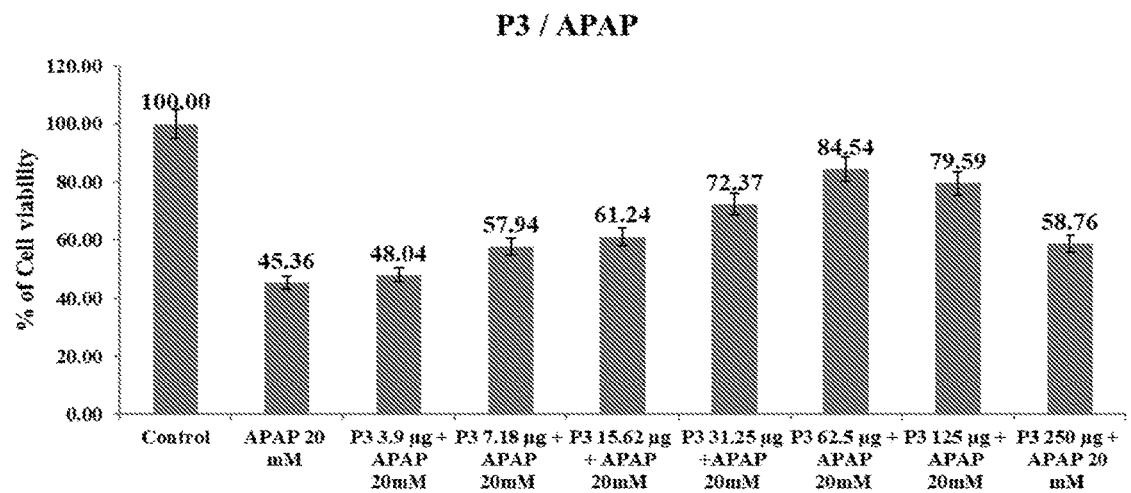
FIG. 4(a) is the bar graph showing the cytotoxicity effects of the processed Synergistic Hepatoprotective composition in HepG2 cells treated with APAP.
Figure 4:
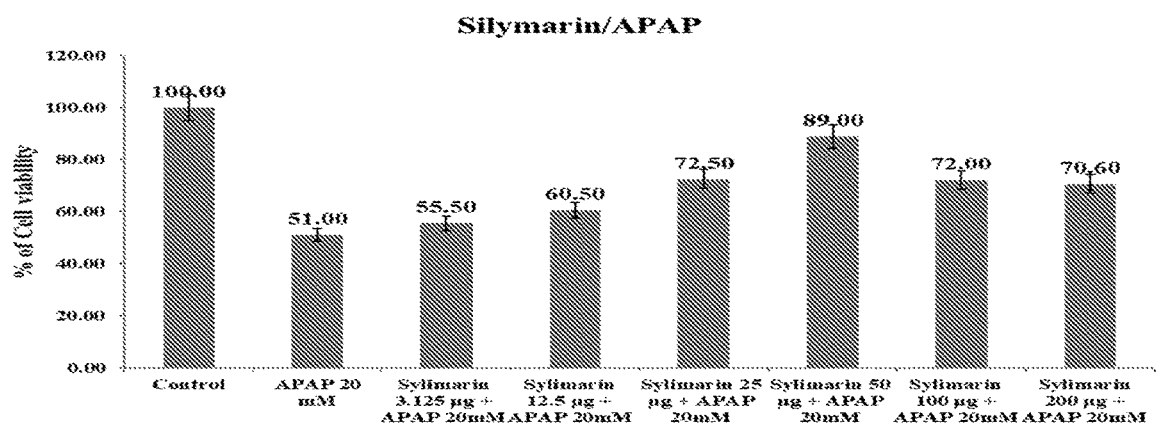
FIG. 4(b) is the bar graph showing the cytotoxicity effects of Silymarin in HepG2 cells treated with APAP.

FIGS. 4(a) and 4(b) show the comparison of cytotoxicity effects of the processed Synergistic Hepatoprotective composition (P3) vs. Silymarin in HepG2 cells treated with APAP.

In this study, APAP-exposure caused significant cytotoxicity in HepG2 cells. Whereas, processed Synergistic Hepatoprotective composition (P3) (62.50 µg) pretreatment significantly prevented APAP-induced cytotoxicity in HepG2 cells; the results were comparable to that of Silymarin (50 µg).

Figure 5A:
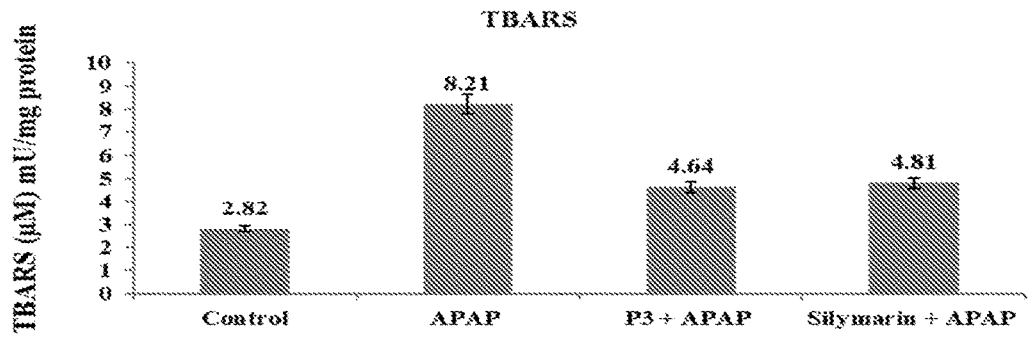
FIG. 5(a) illustrates comparison of the hepatoprotective effects of the processed Synergistic Hepatoprotective composition vs. Silymarin on TBARS activity in HepG2 cells treated with APAP.

D. Hepatoprotective Effects of Processed Synergistic Hepatoprotective Composition Vs. Silymarin on Antioxidant Enzyme Activity on Acetaminophen (APAP)-Induced HepG2 Cells It could be inferred from FIG. 5(a) that level of TBARS increased in APAP-induced HepG2 cells when compared to control treatment. Further, treatment with 62.50 g of the processed synergistic hepatoprotective composition (P3) before APAP induced significantly prevented APAP-mediated TBARS levels. These results were comparable to the effect shown by Silymarin (50 µg).

Figure 5:
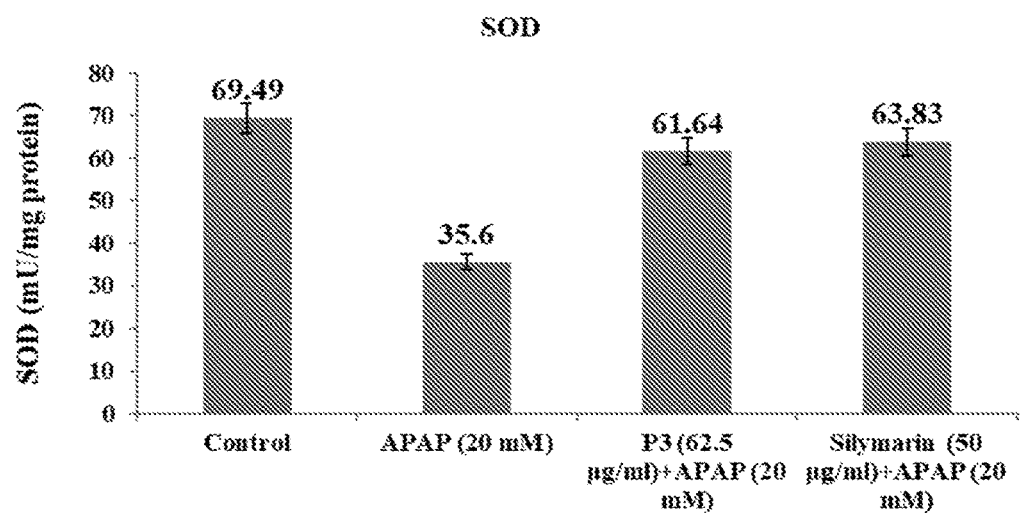
FIG. 5(b) illustrates comparison of the hepatoprotective effects of the processed Synergistic Hepatoprotective composition vs. Silymarin on SOD activity in HepG2 cells treated with APAP.
FIG. 5(c) illustrates comparison of the hepatoprotective effects of the processed Synergistic Hepatoprotective composition vs. Silymarin on GSH levels in HepG2 cells treated with APAP.
Figure 5:
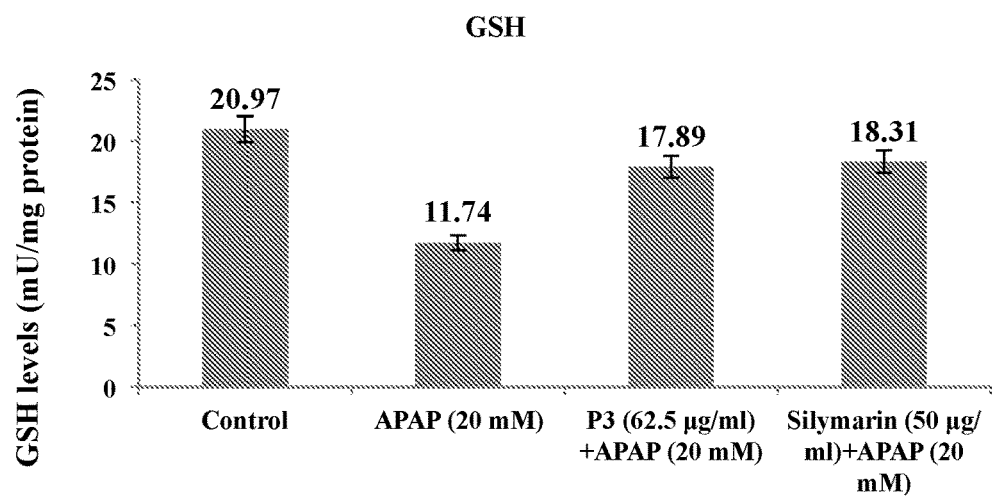

Antioxidants act as a primary defense against free radicals. APAP induced HepG2 cells significantly decreased cellular antioxidant status due to excessive ROS generation. Conversely, treatment with 62.50 g of the processed synergistic hepatoprotective composition (P3) and 50 g of Silymarin concentrations given before inducing APAP significantly prevented APAP-induced loss of antioxidant status (SOD and GSH levels) in HepG2 cells as seen in FIGS. 5(*b*) and (*c*).

Figure 6:
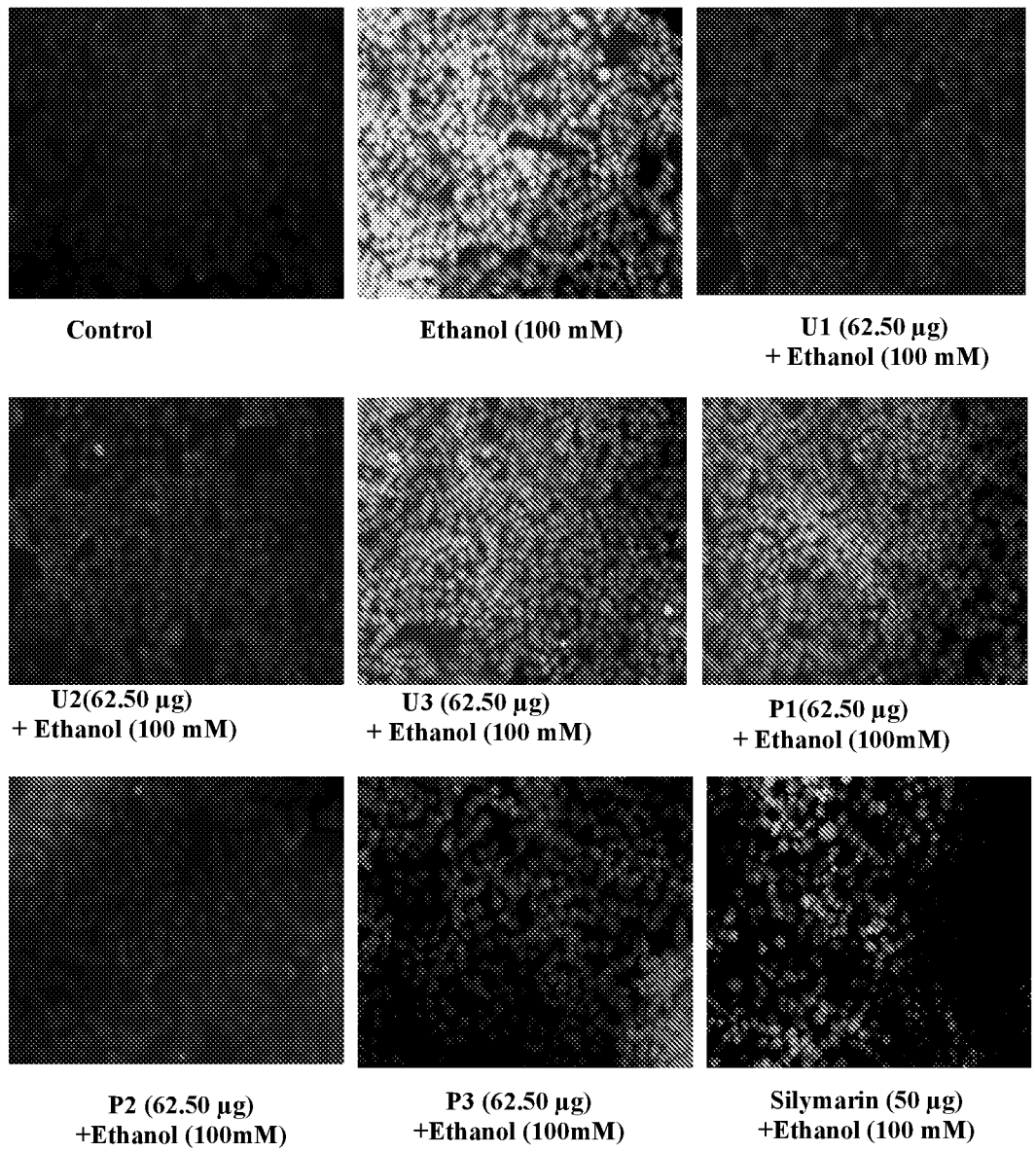
FIG. 6 illustrates the comparison of the impact of the unprocessed and processed Synergistic Hepatoprotective composition vs. Silymarin on ethanol induced intracellular ROS generation in HepG2 cells.

E. Impact of the Unprocessed and Processed Synergistic Hepatoprotective Composition Vs. Silymarin on Ethanol-Induced Intracellular ROS Generation It can be inferred from FIG. 6 that ROS levels were increased in HepG2 cells stimulated by ethanol alone compared to untreated control group. Conversely, U1, U2, U3, P1, P2, P3 (62.50 µg/ml) and Silymarin (50 µg/ml) significantly prevented ethanol induced ROS generation in HepG2 cells. The reduction of ROS generation by treatment with 62.50 g/mL of the processed synergistic hepatoprotective composition (P3) was comparable to that of 50 g/mL of Silymarin treatment.

Figure 7:
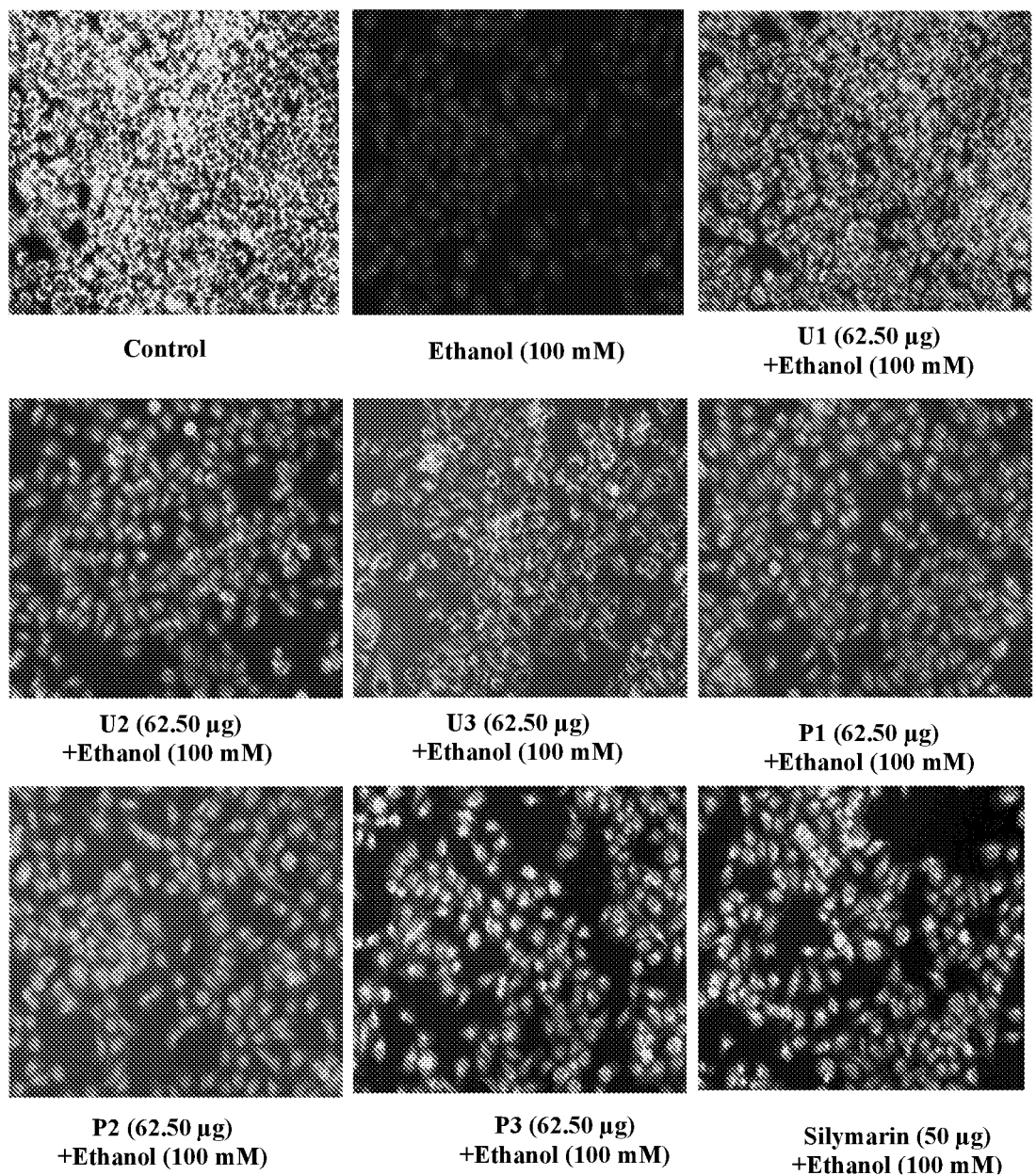
FIG. 7 illustrates the comparison of the effect of the unprocessed and processed Synergistic Hepatoprotective composition vs. Silymarin on ethanol mediated reduction in MMP in HepG2 cells.

F. Effect of the Unprocessed and Processed Synergistic Hepatoprotective Composition Vs. Silymarin on Ethanol-Mediated Reduction in MMP FIG. 7 depicts that the mitochondrial membrane potential was significantly decreased in the cells exposed to ethanol 100 mM for 24 hrs. as compared to control. The depolarization of mitochondria membrane potential induced by the damage of the outer membrane resulted in the loss of the dye from the mitochondria and a decrease in intracellular fluorescence as compared to control. Conversely, pre-treatment with U1, U2, U3, P1, P2 and P3 at 62.50 g/mL and 50 g/mL Silymarin for 24 hours attenuated ethanol induced mitochondrial membrane depolarization which is revealed by increase in fluorescent intensity.

The results indicated that the processed synergistic hepatoprotective composition (P3) was able to significantly increase intracellular fluorescence, thereby indicating a positive effect in prevention of depolarization of the mitochondria membrane potential of the cells and these results were comparable to the effects of the known hepatoprotective agent Silymarin.

Figure 8:
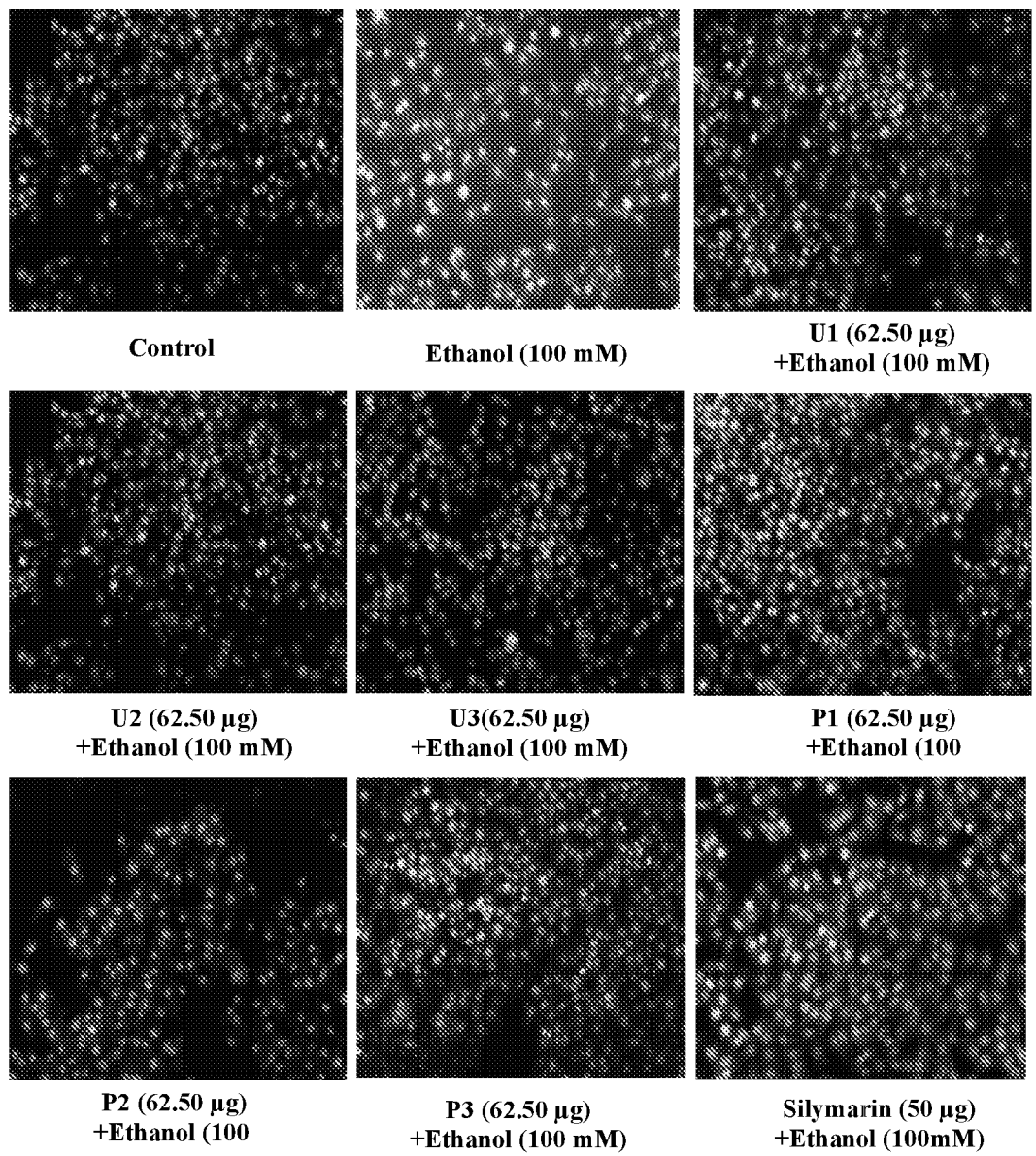
FIG. 8 illustrates the comparison of the effect of the unprocessed and processed Synergistic Hepatoprotective composition vs. Silymarin on ethanol induced nuclear apoptosis in HepG2 cells.

G. Effect of Unprocessed and Processed Synergistic Hepatoprotective Composition Vs. Silymarin on Ethanol-Induced Nuclear Apoptosis FIG. 8 shows the fluorescence microscopy morphological changes in control and Ethanol-induced HepG2 cells after staining with AO/EtBr. The figure is depicting the Photomicrograph which is showing the effect of processed synergistic hepatoprotective composition (P3) 62.50 µg and silymarin 50 µg on Ethanol 100 mM-induced apoptotic morphological changes in HepG2 cells. It can be seen that the processed synergistic hepatoprotective composition (P3) inhibited apoptosis as stained by AO/EtBr staining in HepG2cells which was comparable with the effect shown by Silymarin.

Figure 9:
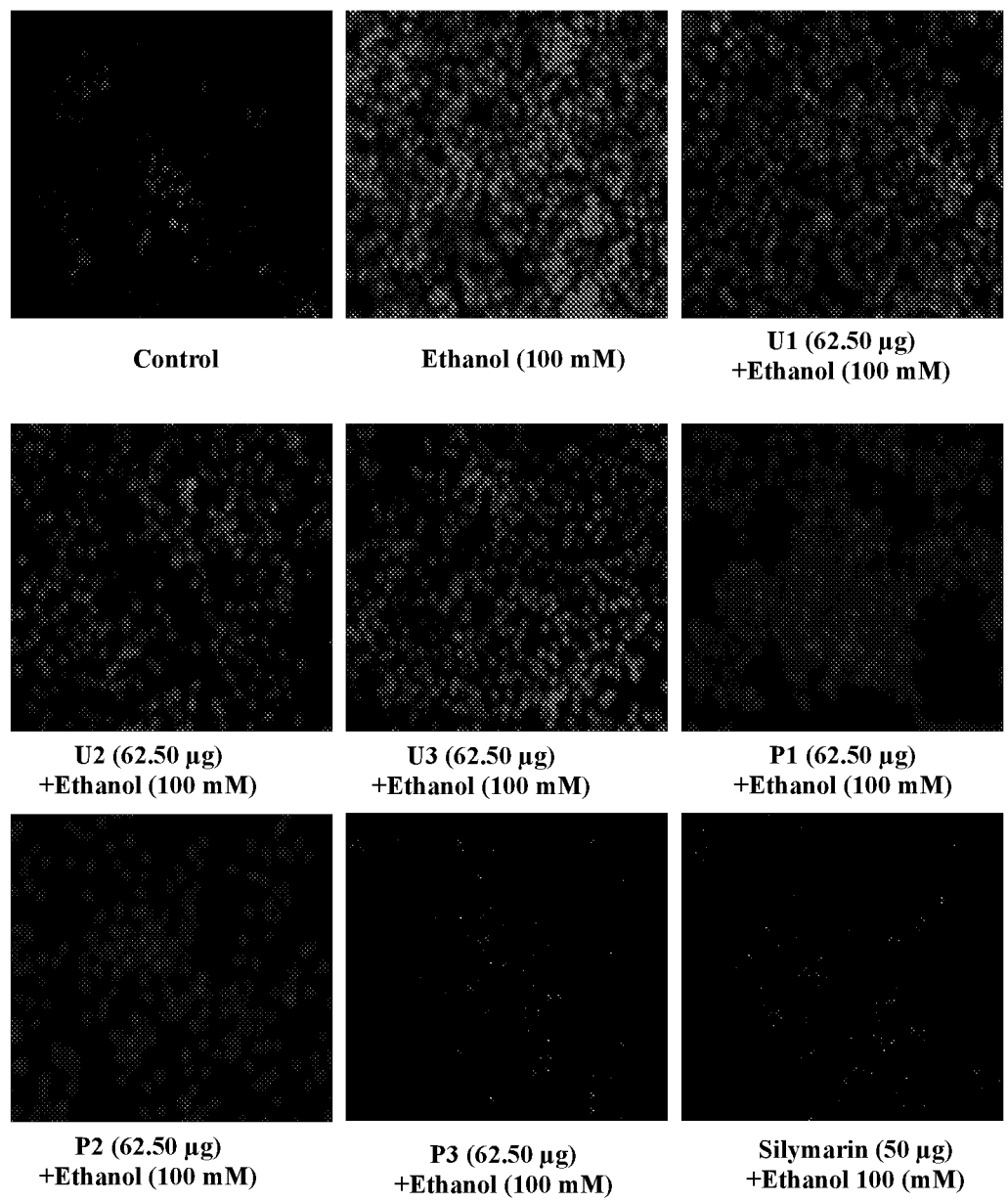
FIG. 9 illustrates the comparison of the effect of the unprocessed and processed Synergistic Hepatoprotective composition vs. Silymarin on ethanol induced nuclear fragmentation in HepG2 cells.

H. Effect of Unprocessed and Processed Synergistic Hepatoprotective Composition Vs. Silymarin on Ethanol-Induced Nuclear Fragmentation HepG2 cells treated with 100 mM ethanol caused nuclear condensation and fragmentation as shown in FIG. 9. It can be seen that both the processed synergistic hepatoprotective composition (P3) and Silymarin treatment prior to ethanol exposure reduced the nuclear condensation and fragmentation which might be due to their strong radical scavenging property.

Figure 10:
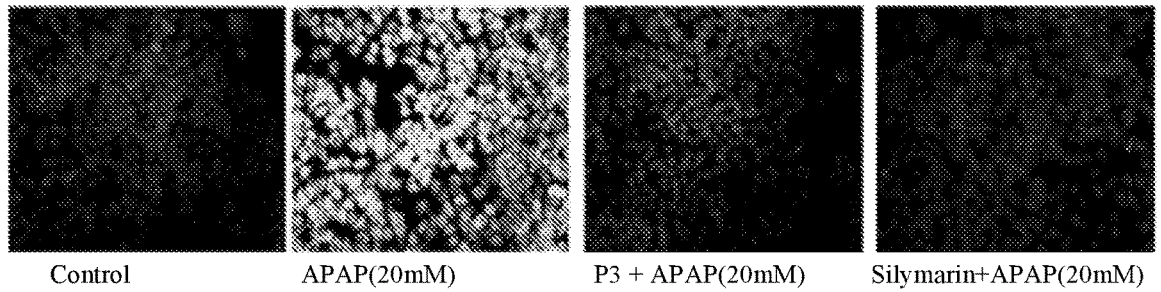
FIG. 10 illustrates the comparison of the impact of the processed Synergistic Hepatoprotective composition vs. Silymarin on APAP-induced intracellular ROS generation in HepG2 cells.

I. Impact of Processed Synergistic Hepatoprotective Composition Vs. Silymarin on APAP-Induced Intracellular ROS Generation HepG2 cells treated with APAP 20 mM caused increase in DCF fluorescence. Pre-treatment of cells with processed synergistic hepatoprotective composition (P3) 62.50 µg/ml decreased the DCF fluorescence and it indicates that it lowered APAP-induced free radical release significantly as compared with APAP alone treated group (FIG. 10).

Figure 11:
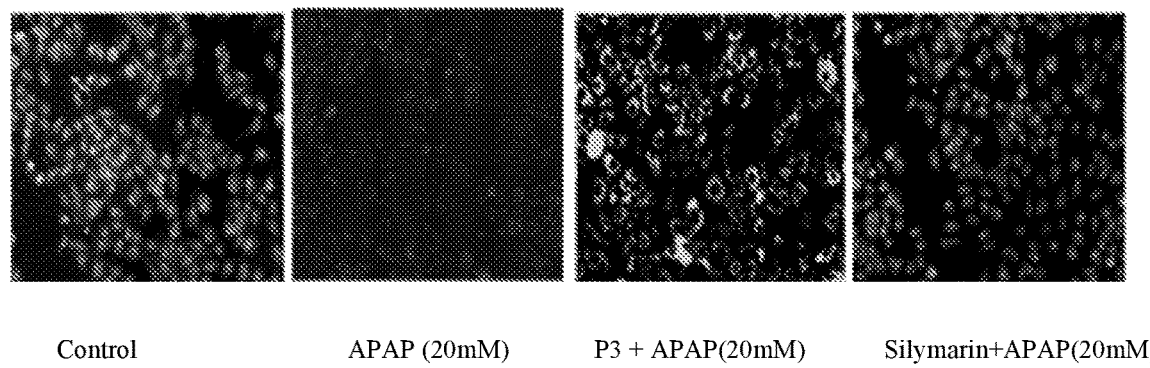
FIG. 11 illustrates the comparison of the effect of the processed Synergistic Hepatoprotective composition vs. Silymarin on APAP-mediated reduction in MMP in HepG2 cells.

J. Effect of Processed Synergistic Hepatoprotective Composition Vs. Silymarin on Acetaminophen (APAP)-Mediated Reduction in MMP The mitochondrial membrane potential ($\Delta\Psi m$) was measured by determining the green fluorescence ratio following the treatment with Rh-123 as shown in FIG. 11. APAP treated cells are polarized and show significant of $\Delta\Psi m$ with decreased green color fluorescence as compared with control. Pre-treatment of cells with processed synergistic hepatoprotective composition (P3) increased green fluorescence indicating a depolarized state of mitochondrial membrane as compared to APAP alone treated cells. Moreover, processed synergistic hepatoprotective composition (P3) and Silymarin showed similar effect respectively.

Figure 12:
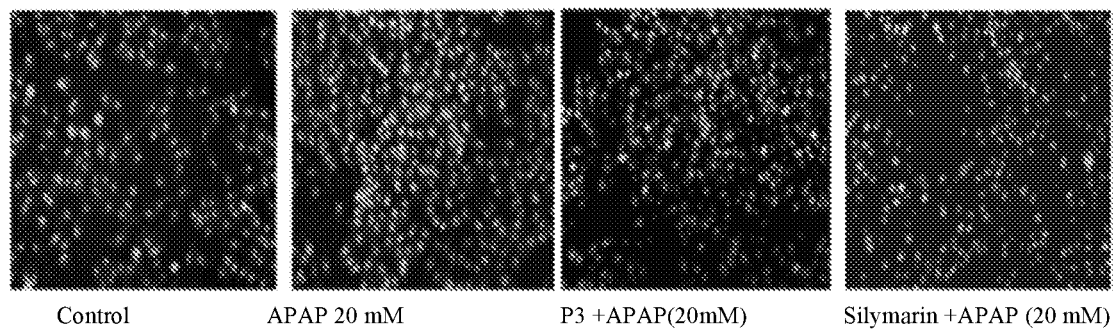
FIG. 12 illustrates the comparison of the effect of the processed Synergistic Hepatoprotective composition vs. Silymarin on APAP induced nuclear apoptosis in HepG2 cells.

K. Effect of Processed Synergistic Hepatoprotective Composition Vs. Silymarin on APAP-Induced Nuclear Apoptosis FIG. 12 shows the Photomicrograph showing the effect of processed Synergistic Hepatoprotective composition (P3) at 62.50 µg and silymarin 50 µg on APAP 20 mM-induced apoptotic morphological changes in HepG2 cells. It can be inferred from FIG. 12 that the processed Synergistic Hepatoprotective composition (P3) inhibited apoptosis as stained by AO/EtBr staining in HepG2cells and the results were comparable to the effect shown by Silymarin.

Figure 13:
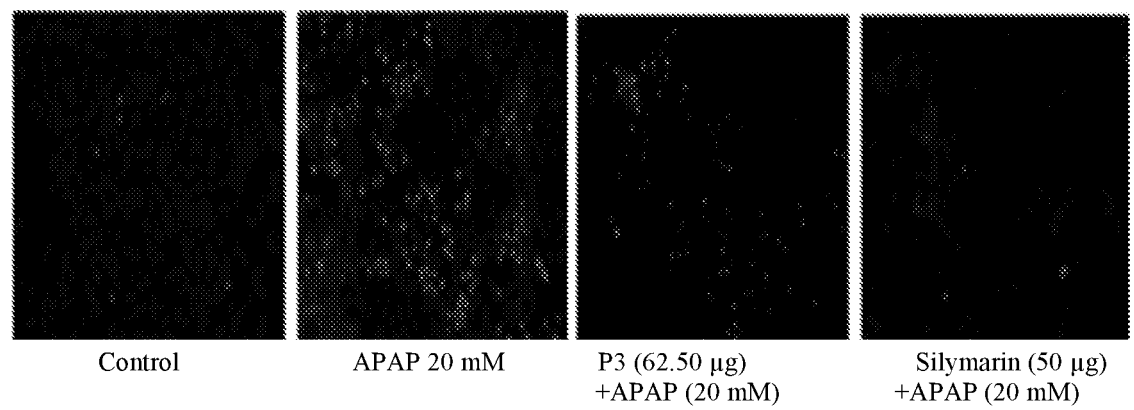
FIG. 13 illustrates the comparison of the effect of the processed Synergistic Hepatoprotective composition vs. Silymarin on APAP induced nuclear fragmentation in HepG2 cells.

L. Effect of Processed Synergistic Hepatoprotective Composition Vs. Silymarin on APAP-Induced Nuclear Fragmentation HepG2 cells treated with 20 mM APAP caused nuclear condensation and fragmentation and morphological changes were observed in cells as seen in FIG. 13. Pre-treatment with processed Synergistic Hepatoprotective composition (P3) and Silymarin prior to APAP exposure inhibited the nuclear condensation and fragmentation as compared to APAP alone treated cells.

Example 6—In-Vivo Studies

Hepatoprotective Effect of Synergistic Hepatoprotective Composition Against Alcohol Induced Liver Damage in Wistar Rats Objectives of the Study:
1. To monitor the effect of Synergistic Hepatoprotective Composition (P3) on alcohol-induced liver damage alterations in the initial and final body weight of experimental rats.
2. To evaluate the effect of Synergistic Hepatoprotective Composition (P3) at different doses on alcohol-induced hepatotoxicity by assessing lipid profile levels TG, TCH, LDL and HDL.
3. To determine the activities of liver marker enzymes AST, ALT, ADH and GGT.
4. To evaluate the effect of Synergistic Hepatoprotective Composition (P3) at different doses on alcohol-induced hepatotoxicity by assessing the lipid peroxidation markers MDA and 4-HNE.

5. To asess inflammatory (TNF-α, IL-6 and IL-1) markers during alcohol-induced hepatotoxicity in rats.

Materials and Methods:

Animals

Male Wistar rats, weighing 130-150 g, procured from Biogen Laboratory Animal Facility, India. Animals were acclimatized under standard vivarium conditions at 25±2° C. with 12 h light: dark cycle. The animals were fed with standard rat chow and water ad libitum. The food was withdrawn 18-24 h before the experiment. The care and use of laboratory animals were done according to the guidelines of the Council Directive CPCSEA, India (MCAS/IAEC/2019/6/9/2/2019) about Good Laboratory Practice on animal experimentation.

Experimental Design and Treatment Schedule:

The experimental male wistar rats were distributed into six groups, each group containing six animals, analyzed for a total experimental period of 28 days and the dosages administered of ethanol, silymarin and the processed synergistic hepatoprotective composition P3 were as follows:

Group 1: Control (vehicle),
Group 2: Ethanol (EtOH) (2.4 mg/kg bw) in 0.9% saline
Group 3: EtOH+Silymarin (200 mg/kg bw)
Group 4: EtOH+P3 2:1 (200 mg/kg/bw)
Group 5: EtOH+P3 −4:1 (200 mg/kg bw)
Group 6: EtOH+P3 −6:1 (200 mg/kg/bw)

Control and ethanol groups received 0.9% saline respectively via gavage needle for 28 days. To examine the hepatoprotective properties of drug treatment, rats were administered silymarin and synergistic hepatoprotective composition (P3), 30 min before ethanol administration for 28 days.

Composition of Animal Feed:

Protein—17.7%, Fat—4.2%, Carbohydrate—50.5%, Fiber—3.4%, Minerals—6.7% and Vitamins—1.7%.

At the 28$^{th}$ day of the study, all animals were anaesthetized using chloroform, blood samples were collected through vain from control and experimental rats. Blood samples were centrifuged at 3000 rpm for 30 min the serum samples were kept in freezer at −20° C. till analysis. The liver of the sacrificed animals were also removed immediately, rinsed properly in ice cold normal saline, blotted dry and weighed, to note the organ weight. A part of the liver tissue was then immediately immersed in appropriate fixative for further histopathological study. The remaining part of the liver was kept for biochemical assay.

Measurement of Liver Weight to Body Weight

Body weight of all animals at the end of the treatment period, along with their liver weight on the day of sacrifice was noted to determine the liver weight on the day of sacrifice was noted to determine the liver weight to final body weight of animals in each group.

Preparation of Tissue Homogenate

A 10% w/v liver tissue homogenate was prepared in ice cold phosphate buffer saline (PBS) containing 1 mM EDTA (pH 7.4), using tissue homogenizer. The homogenate was then centrifuged at 10,000 rpm for 30 minutes, at 4° C. The supernatant thus obtained was used further, for the following biochemical assay of tissue oxidative stress markers.

Biochemical Analysis

The protein content was estimated by the method of Lowry et al. (1951). Aspartate aminotransferase (AST), alanine aminotransferase (ALT), gamma-glutamyltransferase (GGT), triglycerides (TG), total cholesterol (TCH), low density lipoprotein cholesterol (LDL-C), high density lipoprotein cholesterol (HDL-C), malondialdehyde (MDA) and 4-hydroxynonenal (4-HNE) analysis by using commercially available diagnostic kits (Micro clinical lab, Tamil Nadu).

Hepatic ADH Activities

Alcohol dehydrogenase (ADH) activity was determined by the method of Bonnichsen and Brink (1955). Briefly, ADH activity was measured in 50 mM glycine (pH 9.6), 0.8 mM NAD, 3 mM ethanol and 50 µl of cytosolic fraction in a final volume of 1 ml. Enzyme activity was measured at 340 nm and the activity was calculated as nmol NADH formed/min/mg protein using a molar extinction co-efficient of $6.22 \times 10^6$ M−1 cm−1.

Cytokine Assessment

Assessment of pro-inflammatory cytokines, viz., tumour necrotic factor alpha (TNF-α) and interleukin 6 (IL-6) and Interleukin 1 (IL-1) was also carried out using commercially available ELISA kit and expressed in picogram per millilitre (pg/mL) (Biovision, Milpitas, CA, USA).

Histopathological Studies

A part of the rat hepatic tissue from control and treated animals were directly fixed in 10% formalin buffer and embedded in paraffin after regular clearing with saline and dehydration. After all the process, 3-5 µm thick sections was then prepared from the tissue blocks using microtome. The tissue sections were then stained with hematoxylin and eosin (H&E). The tissue sections were observed under microscope and the correspondent images were captured using a digital camera attached to it.

Statistical Analysis

Each experiment was repeated at least three times. Data are presented as means±S.E. Significance of mean values of different parameters between the treated groups were analysed using one way post hoc tests (Tukey's HSD test) of analysis of variances (ANOVA) after ascertaining the homogeneity of variances between the treatment groups. Statistical tests were performed using SPSS software version 20.0. A value of $p<0.05$ was considered statistically significant.

Results:

A. Effect of the Processed Synergistic Hepatoprotective Composition on General Observation Body Weights Table 2 shows the intake of levels of water and food in the control and experimental rats. There was no difference in food and water consumptions between groups of control and experimental rats during the entire period of the study.

Table 3 and 3a show the effect of ethanol and the processed synergistic hepatoprotective composition (P3) of the present invention on body weight, weight gain and growth rate and liver weight in control and experimental groups of rats, respectively. The body weight was decreased whereas liver weight increased significantly ($P<0.05$) in ethanol-induced rats than that of untreated control (Group 1) rats where as it appeared near normal in rats that were treated with processed synergistic hepatoprotective composition (P3) (Groups 4-6) when compared with Group 2 rats. In Group 2 rats the body weight, weight gain and growth rate was significantly reduced ($p<0.05$) when compared with Group 1 rats. Treatment with the synergistic hepatoprotective composition of the present invention (P3) having curcuminoids and lutein in different ratios also showed protection against the loss in body weight induced by ethanol treatment rats and was comparable to the effects shown by Silymarin.

TABLE 2

Intake levels of water and food in the control and experimental rats in each group (n = 6).

| Groups | Treatments | Dose per kg | No. of animals | Water intake (ml) | Food intake (gm) |
|---|---|---|---|---|---|
| 1 | Control | 10 ml | 6 | 118.02 ± 8.99 | 25.05 ± 1.91 |
| 2 | EtOH | 2.4 gm | 6 | 93.78 ± 7.14 | 17.02 ± 1.36 |
| 3 | EtOH + Silymarin | 200 mg | 6 | 103.08 ± 7.66 | 25.11 ± 1.55 |
| 4 | EtOH + P3-2:1 | 200 mg | 6 | 106.06 ± 8.15 | 24.06 ± 1.91 |
| 5 | EtOH + P3-4:1 | 200 mg | 6 | 104.07 ± 8.00 | 26.03 ± 2.06 |
| 6 | EtOH + P3-6:1 | 200 mg | 6 | 106.23 ± 8.16 | 27.12 ± 2.14 |

*Values are given as mean SD of each group.

TABLE 3

Initial and final body weight changes and growth rate of control and experimental rats in each groups (n = 6).

| Groups | Treatments | Dose per kg | Initial body weight (g) | Final body weight (g) | Weight gain (g) | Growth rate (g) |
|---|---|---|---|---|---|---|
| 1 | Control | 10 ml | 147.10 ± 11.20 | 178.10 ± 13.56 | 31.00 ± 2.36 | 1.10 ± 0.08 |
| 2 | EtOH | 2.4 gm | 148.55 ± 11.31 | 159.41 ± 12.14 | 10.86 ± 0.83 | 0.38 ± 0.03 |
| 3 | EtOH + Silymarin | 200 mg | 151.10 ± 11.57 | 174.42 ± 13.35 | 23.32 ± 1.79 | 0.83 ± 0.06 |
| 4 | EtOH + P3-2:1 | 200 mg | 149.51 ± 11.39 | 172.44 ± 13.13 | 22.93 ± 1.75 | 0.82 ± 0.06 |
| 5 | EtOH + P3-4:1 | 200 mg | 147.03 ± 11.20 | 173.61 ± 13.22 | 26.58 ± 2.02 | 0.94 ± 0.07 |
| 6 | EtOH + P3-6:1 | 200 mg | 147.89 ± 11.26 | 176.06 ± 13.41 | 28.17 ± 2.15 | 1.00 ± 0.08 |

*Values are given as mean SD of each group.

TABLE 3a

Effect of synergistic hepatoprotective composition against ethanol induced changes in the liver weight of control and experimental rats in each group (n = 6)

| Groups | Treatments | Dose per kg | Liver weight |
|---|---|---|---|
| 1 | Control | 10 ml | 5.13 ± 0.39 |
| 2 | EtOH | 2.4 gm | 7.21 ± 0.55 |
| 3 | EtOH + Silymarin | 200 mg | 5.30 ± 0.41 |
| 4 | EtOH + P3-2:1 | 200 mg | 5.82 ± 0.44 |
| 5 | EtOH + P3-4:1 | 200 mg | 5.57 ± 0.42 |
| 6 | EtOH + P3-6:1 | 200 mg | 5.42 ± 0.41 |

*Values are given as mean SD of each group.

B. Effect of the Processed Synergistic Hepatoprotective Composition of the Present Invention on Changes in Liver Function Marker Enzymes Table 4 indicates the alteration in the activities of liver marker enzymes in the control and experimental rats. Administration of ethanol significantly increased (p<0.05) AST, ALT and GGT levels respectively. Eventually co-treatment with the processed synergistic hepatoprotective composition of the present invention (P3) having curcuminoids and lutein in the ratio of 4:1 and 6:1 (Group 5 and 6) at a dose of 200 mg/Kg significantly (p<0.05) reduced the elevated levels of AST, ALT and GGT as compared to ethanol treated rats. Further, the results shown by the processed synergistic hepatoprotective composition of the present invention (P3) having curcuminoids and lutein in the ratios of 4:1 and 6:1 were comparable with the results of Silymarin.

TABLE 4

Effect of the synergistic hepatoprotective composition (P3) against ethanol induced changes in liver function marker enzymes of control and experimental rats in each groups (n = 6).

| Groups | Treatments | Dose per kg | AST (U/L) | ALT (U/L) | GGT (U/L) |
|---|---|---|---|---|---|
| 1 | Control | 10 ml | 166.05 ± 12.64 | 11.05 ± 0.84 | 2.31 ± 0.18 |
| 2 | EtOH | 2.4 gm | 216.34 ± 16.47 | 23.03 ± 1.75 | 7.93 ± 0.60 |
| 3 | EtOH + Silymarin | 200 mg | 176.61 ± 13.52 | 13.32 ± 1.02 | 2.80. ± 0.21 |
| 4 | EtOH + P3-2:1 | 200 mg | 190.56 ± 14.51 | 18.63 ± 1.42 | 5.07 ± 0.39 |
| 5 | EtOH + P3-4:1 | 200 mg | 178.09 ± 13.56 | 16.39 ± 1.25 | 3.29 ± 0.25 |
| 6 | EtOH + P3-6:1 | 200 mg | 175.44 ± 13.36 | 14.05 ± 1.07 | 2.50 ± 0.19 |

*Values are given as mean SD of each group.

Ethanol consumption enhances the ratio of NADH/NADb in hepatocytes which causes disruption of beta-oxidation of fatty acids in mitochondria leading to steatosis. Alcohol also increases the lipid transport to the liver from the small intestine leading to enhanced mobilization of fatty acids from adipose tissue which is taken up by the liver (16). This causes damage to cell membrane of hepatocytes leading to augmented levels of transaminases (Alanine aminotransferase (ALT) and AST (Aspartate aminotransferase)) in blood stream. Gammaglutamyl transferase (GGT) has a key role in preserving intracellular homeostasis of oxidative stress which protects cells against oxidative damage. It is present in cell membrane and is set free in circulation when cell membrane is damaged.

The present findings revealed that ethanol administration triggered a significant increase in serum AST, ALT and GGT enzyme activities compared with the control group. These increases may be due to liver damage induced by alcohol intoxication. Administration of the processed synergistic hepatoprotective composition (P3) of the present invention with different ratios of its components viz. Curcuminoids and Lutein effectively assuaged the increased levels of the serum enzymes, caused by alcohol intake and led to a subsequent recovery towards normalization that was comparable to the control group animals.

C. Effect of the Processed Synergistic Hepatoprotective Composition of the Present Invention on Ethanol Induced Changes in Lipid Profile Table 5 shows the comparison of the effect of the processed synergistic hepatoprotective composition (P3) having different ratios of its components viz. Curcuminoids and Lutein on ethanol-induced hepatotoxicity by assessing the lipid profile viz. levels of TG, TCH, LDL-C and HDL-C levels in the control and experimental rats.

It can be inferred from Table 5 that treatment with ethanol also disrupts the lipid profile homeostasis of the body, leading to an increase in TG, TCH and LDL-C levels respectively, along with a simultaneous decrease in HDL-C level ($p<0.05$). Co-treatment with the processed synergistic hepatoprotective composition of the present invention (P3) significantly reversed the above changes to near normal values ($p<0.05$). During ethanol metabolism, large amounts of reduced nicotinamide-adenine dinucleotide (NADH) is produced, thus, inhibiting Krebs cycle and oxidation of fatty acid, which favours liver steatosis and serum hyperlipidaemia (17).

In addition, ethanol group also shows increase in the levels of TCH, TG, LDL along with a simultaneous decrease in HDL level. However, treatment with the processed synergistic hepatoprotective composition (P3) attenuated the above changes in lipid profile levels. The synergistic hepatoprotective composition of the present invention (P3) is therefore, effective in maintaining the lipid profile. Also, it is effective in maintaining healthy cholesterol levels and healthy LDL/HDL ratio.

The hypocholesterolemic activity of the processed synergistic hepatoprotective composition (P3) treated animals may be attributed to increased hepatic clearance of cholesterol through elevated serum HDL levels, or to down regulation of cholesterol bio-synthetic enzyme, HMG-CoA reductase (18).

TABLE 5

Comparison of the effect of synergistic hepatoprotective composition at different doses on Lipid Profile

| Groups | Treatments | Dose per kg | TG (mg/dL) | TCH (mg/dL) | LDL-C (mg/dL) | HDL-C (mg/dL) |
|---|---|---|---|---|---|---|
| 1 | Control | 10 ml | 126.23 ± 9.61 | 45.11 ± 3.43 | 11.58 ± 0.88 | 14.03 ± 1.07 |
| 2 | EtOH | 2.4 gm | 155.36 ± 11.83 | 79.53 ± 6.06 | 29.16 ± 2.22 | 09.36 ± 0.71 |
| 3 | EtOH + Silymarin | 200 mg | 129.43 ± 9.91 | 54.09 ± 4.14 | 15.38 ± 1.18 | 12.39 ± 0.95 |
| 4 | EtOH + P3-2:1 | 200 mg | 135.63 ± 10.33 | 63.44 ± 4.83 | 21.09 ± 1.61 | 11.07 ± 0.84 |
| 5 | EtOH + P3-4:1 | 200 mg | 131.51 ± 10.01 | 52.04 ± 3.96 | 17.13 ± 1.30 | 12.32 ± 0.94 |
| 6 | EtOH + P3-6:1 | 200 mg | 128.03 ± 9.75 | 41.32 ± 3.15 | 15.50 ± 1.18 | 13.58 ± 1.03 |

*Values are given as mean SD of each group.

D. Effect of the Processed Synergistic Hepatoprotective Composition of the Present Invention on Ethanol Induced Changes in Liver ADH, MDA and 4-HNE Table 6 shows the comparison of the effect of the processed synergistic hepatoprotective composition of the present invention (P3) at different ratios of its components viz. Curcuminoids and Lutein in ratios of 2:1, 4:1 and 6:1 on ethanol induced changes in liver on the levels of ADH, MDA and 4-HNE. Ethanol treated group (Group 2) showed significant increase in ADH, MDA and 4-HNE levels as compared to control group. The increased level of ADH, MDA and 4-HNE in ethanol control group indicated the presence of lipid profile of liver cells, which was due to the toxic effect of ethanol.

Co-treatment with the processed synergistic hepatoprotective composition of the present invention (P3) having curcuminoids and lutein in the ratio of 4:1 and 6:1 (Group 5 and 6) at a dose of 200 mg/Kg significantly ($p<0.05$) reduced the elevated levels of ADH, MDA and 4-HNE as compared to ethanol treated rats.

TABLE 6

Comparison of the levels of ADH, MDA and 4-HNE in the liver tissue of control and experimental rats in each groups (n = 6).

| Groups | Treatments | Dose pe rkg | ADH (nmol/mg protein) | MDA (nmol/mg protein) | 4-HNE (nmol/mg protein) |
|---|---|---|---|---|---|
| 1 | Control | 10 ml | 6.30 ± 0.48 | 4.23 ± 0.32 | 1.53 ± 0.12 |
| 2 | EtOH | 2.4 gm | 8.45 ± 0.64 | 9.25 ± 0.70 | 1.95 ± 0.15 |
| 3 | EtOH + Silymarin | 200 mg | 6.50 ± 0.50 | 4.69 ± 0.36 | 1.54 ± 0.12 |
| 4 | EtOH + P3-2:1 | 200 mg | 7.72 ± 0.59 | 6.38 ± 0.49 | 1.66 ± 0.13 |
| 5 | EtOH + P3-4:1 | 200 mg | 6.81 ± 0.52 | 4.97 ± 0.38 | 1.58 ± 0.12 |
| 6 | EtOH + P3-6:1 | 200 mg | 6.43 ± 0.49 | 4.71 ± 0.36 | 1.55 ± 0.12 |

*Values are given as mean SD of each group.

E. Effect of the Processed Synergistic Hepatoprotective Composition of the Present Invention on Ethanol Induced Changes in Cytokine Levels Table 7 indicates the effect of the processed synergistic hepatoprotective composition of the present invention (P3) on ethanol induced changes in cytokine levels. It can be seen that administration of ethanol resulted in significant increase in serum TNF-α, IL-6 and IL-1 levels compared to control Group 1 ($p<0.001$). Table 7 shows that serum TNF-α, IL-6 and IL-1 levels increased respectively in ethanol treated Group 2. Co-treatment with the processed synergistic hepatoprotective composition (P3) caused a marked decrease in serum TNF-α, IL-6 and IL-1 levels as can be seen in the results of Groups 4 to 6.

TABLE 7

Effect of the Hepatoprotective composition of the present invention on ethanol induced changes in cytokine levels

| Groups | Treatments | Dose per kg | TNF-α (pg/mL) | IL-6 (pg/mL) | IL-1 (pg/mL) |
|---|---|---|---|---|---|
| 1 | Control | 10 ml | 185.16 ± 14.10 | 113.53 ± 8.64 | 169.58 ± 12.91 |
| 2 | EtOH | 2.4 gm | 358.57 ± 27.30 | 195.11 ± 14.86 | 397.09 ± 30.24 |
| 3 | EtOH + Silymarin | 200 mg | 187.61 ± 14.36 | 115.39 ± 8.83 | 173.47 ± 13.28 |
| 4 | EtOH + P3-2:1 | 200 mg | 276.44 ± 21.05 | 145.66 ± 11.09 | 211.14 ± 16.08 |
| 5 | EtOH + P3-4:1 | 200 mg | 186.15 ± 14.17 | 127.54 ± 9.71 | 189.39 ± 14.42 |
| 6 | EtOH + P3-6:1 | 200 mg | 189.49 ± 14.43 | 117.55 ± 8.95 | 175.35 ± 13.35 |

*Values are given as mean SD of each group.

F. Histopathological Analysis of Liver Tissues

Figure 14:
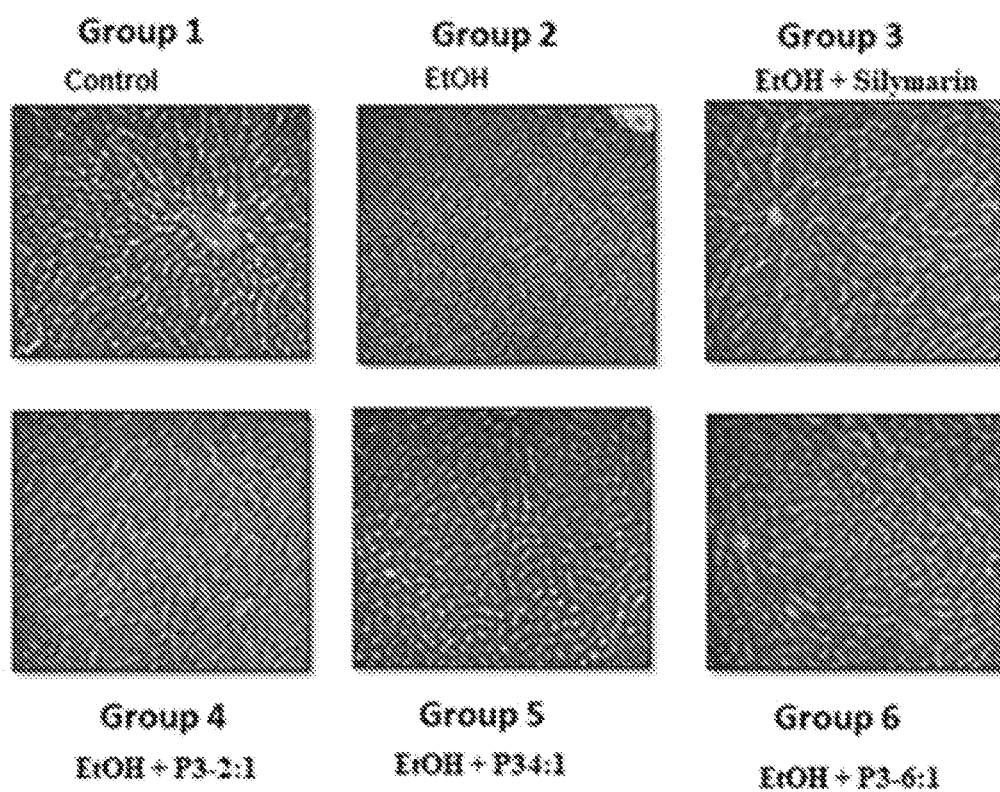
FIG. 14 illustrates the effects of the processed Synergistic Hepatoprotective composition vs. Silymarin on ethanol-induced histopathology changes in the liver of rats at 28 days of study.

The histological features shown in FIG. 14, indicate a normal liver lobular architecture and cell structure of the livers in the control rats. There were no pathological changes in the healthy control livers. In ethanol induced rats i.e. Group 2, the extent of liver damage was evaluated by histological analysis after continuation of 2 gm/kg bw, ethanol intake for 4 weeks. For instance, hepatic sinus dilation, extrusion and atrophy of cords were observed in the centrilobular hepatocytes, possibly suggesting hepatocyte regeneration; slight infiltration of mononuclear cells and necrotic cells were observed around the central vein. Vacuolar changes and possibly fatty degeneration were observed in the centrilobular region. In brief, swelling, hydropic degeneration, and vacuolation of hepatic cells became prominent in the centrilobular region, which reflected early biochemical and pathological changes caused by alcoholic liver injury.

Ethanol treated Group 2 rats showed inflammatory response around the central vein with vacuolar degeneration and necrosis. In Groups 3, 4 and 5, the hepatic tissue showed lesser vacuolar degeneration and lesser inflammatory response around the central vein. Group 6 liver tissue showed almost normal architecture. Therefore, histopathological changes induced by ethanol were significantly improved by the processed synergistic composition of the present invention (P3), especially in the composition of the present invention (P3) having curcuminoids and lutein in the ratio of 4:1 and 6:1 (Group 5 and 6), which significantly alleviated steatosis in the liver and showed obvious improvements compared with the Ethanol-treated group.

Conclusion of Study

In conclusion, the in-vivo studies demonstrate that the processed synergistic hepatoprotective composition of the present invention (P3) is effective in normalizing and maintaining the lipid profile. Also, it is effective in maintaining healthy cholesterol levels and a healthy LDL/HDL ratio. Further, the synergistic hepatoprotective composition of the present invention is effective in normalizing and maintaining the levels of the serum enzymes viz. AST, ALT, ADH and GGT. The study on the assessment of lipid peroxidation markers MDA and 4-HNE also showed that the synergistic hepatoprotective composition is effective in reducing the lipid peroxidation which may be caused by various factors such as unhealthy dietary patterns, high consumption of PUFA and alcohol consumption. Furthermore, the synergistic hepatoprotective composition of the present invention was found to be effective in reducing the serum pro-inflammatory cytokine (TNF-α, IL-6 and IL-1) levels which are markers of inflammatory response of liver. These serum pro-inflammatory cytokines (TNF-α, IL-6 and IL-1) are believed to be strongly elevated in patients with non-alcoholic and alcoholic fatty liver disease.

It is also inferred from the results that the synergistic hepatoprotective composition of the present invention is helpful in protecting the liver against ethanol induced toxicity possibly through lipid lowering and hepatoprotective activity. Further, the composition beneficially ameliorated the ethanol induced liver toxicity by preserving the liver's status in terms of its antioxidant status, reducing the levels of lipid profile, liver enzymatic markers and anti-inflammatory activity as well against chronic alcohol exposure.

The histopathological analysis of liver tissues indicated that the changes induced by ethanol were significantly improved by the processed synergistic composition of the present invention (P3), especially in the composition of the present invention (P3) having curcuminoids and lutein in the ratio of 4:1 and 6:1.

While particular embodiments of the synergistic hepatoprotective composition of present invention have been illustrated and described, it would be obvious to those skilled in the art that various other changes and modifications can be made within departing from the spirit and scope of the invention. It is therof intended to cover in the appended claims such changes and modifications that are within the scope of the invention.

We claim:

1. A composition for hepatoprotection consisting of particles of Curcuminoids and lutein in a ratio in the range of 2:1 to 6:1 wherein the composition is processed to a particle size in the range of $D_{50}$-0.36 μm to 5 μm and $D_{90}$ in the range of 0.60 μm to 10 μm, and wherein each particle of the composition consisting of Curcuminoids and Lutein with said particle size exhibits a synergistic hepatoprotection activity.

2. The composition as claimed in claim 1 wherein the Curcuminoids and lutein are present in a ratio in the range of 4:1 to 6:1.

3. The composition as claimed in claim 1 wherein the curcuminoids and lutein are present in their purified form and wherein the purity of the curcuminoids is in the range of 80-95% and the purity of lutein is in the range of 70-85%.

4. The composition as claimed in claim 1 wherein the said composition is effective in protecting the liver against liver damage or liver toxicity.

5. The composition as claimed in claim 4 wherein the said composition is effective in protecting the liver against liver toxicity by suppressing the oxidative stress injury caused on the cells.

6. The composition as claimed in claim 4 wherein the said composition is effective in protecting against liver peroxidation by decreasing the production of Thiobarbituric acid reactive species (TBARS) Malondialdehyde (MDA) in the affected cells.

7. The composition as claimed in claim 4 wherein the said composition is effective in protecting the liver against liver toxicity by increasing the levels of non-enzymatic antioxidants Glutathione reductase (GSH) and superoxide dismutase (SOD) in the affected cells.

8. The composition as claimed in claim 4 wherein the said composition is effective in protecting the liver against liver toxicity by preventing reactive oxygen species (ROS) generation in the affected cells.

9. The composition as claimed in claim 4 wherein the said composition is effective in protecting the liver against liver toxicity by preventing nuclear apoptosis, nuclear fragmentation of cells and preventing the depolarization of mitochondrial membrane of cells, in the affected cells.

10. The composition as claimed in claim 4 wherein the said composition is effective in reducing the pro-inflammatory cytokine (TNF-α, IL-6 and 1L-1) levels which is beneficial in reduction of the inflammatory response of liver due to alcoholic and non-alcoholic fatty liver disease which may be caused by unhealthy dietary patterns.

11. The composition as claimed in claim 1 wherein the said composition may be taken/ingested on a regular basis as supplement or before, during or after intake of fatty foods, drugs and/or alcohol.

* * * * *